(12) United States Patent
Whayne et al.

(10) Patent No.: US 10,610,208 B2
(45) Date of Patent: *Apr. 7, 2020

(54) SUBXYPHOID EPICARDIAL ABLATION

(71) Applicant: Atricure, Inc., Mason, OH (US)

(72) Inventors: James G. Whayne, Cary, NC (US); Sidney D. Fleischman, Durham, NC (US)

(73) Assignee: AtriCure, Inc., Mason, OH (US)

( * ) Notice: Subject to any disclaimer, the term of this patent is extended or adjusted under 35 U.S.C. 154(b) by 403 days.

This patent is subject to a terminal disclaimer.

(21) Appl. No.: 14/864,697

(22) Filed: Sep. 24, 2015

(65) Prior Publication Data
US 2016/0242750 A1    Aug. 25, 2016

Related U.S. Application Data

(63) Continuation of application No. 13/107,747, filed on May 13, 2011, now Pat. No. 9,173,705.

(60) Provisional application No. 61/334,499, filed on May 13, 2010, provisional application No. 61/334,519, filed on May 13, 2010.

(51) Int. Cl.
| | | |
|---|---|---|
| *A61B 18/02* | (2006.01) |
| *A61B 17/00* | (2006.01) |
| *A61B 17/32* | (2006.01) |
| *A61B 18/14* | (2006.01) |
| *A61B 6/12* | (2006.01) |
| *A61B 18/00* | (2006.01) |
| *A61B 90/00* | (2016.01) |

(52) U.S. Cl.
CPC .. *A61B 17/00234* (2013.01); *A61B 17/32002* (2013.01); *A61B 18/148* (2013.01); *A61B 18/1492* (2013.01); *A61B 6/12* (2013.01); *A61B 2017/003* (2013.01); *A61B 2017/00247* (2013.01); *A61B 2017/00858* (2013.01); *A61B 2017/320004* (2013.01); *A61B 2017/320012* (2013.01); *A61B 2018/00005* (2013.01); *A61B 2018/00285* (2013.01); *A61B 2018/00291* (2013.01); *A61B 2018/00351* (2013.01); *A61B 2018/00773* (2013.01); *A61B 2018/1435* (2013.01); *A61B 2090/065* (2016.02); *A61B 2218/002* (2013.01); *A61B 2218/007* (2013.01)

(58) Field of Classification Search
CPC ........ A61B 17/00234; A61B 17/32002; A61B 18/148; A61B 18/1492; A61B 2017/00247; A61B 2017/003; A61B 2017/00858; A61B 2017/320004; A61B 2017/320012; A61B 2018/00005; A61B 2018/00285; A61B 2018/00291; A61B 2018/00351; A61B 2018/00773; A61B 2018/1435; A61B 2090/065; A61B 2218/002; A61B 2218/007; A61B 6/12

See application file for complete search history.

(56) References Cited

U.S. PATENT DOCUMENTS

| | | |
|---|---|---|
| 5,370,134 A | 12/1994 | Chin et al. |
| 5,522,790 A | 6/1996 | Moll et al. |
| 6,190,382 B1 | 2/2001 | Ormsby et al. |
| 6,237,605 B1 | 5/2001 | Vaska et al. |

(Continued)

*Primary Examiner* — Daniel W Fowler
(74) *Attorney, Agent, or Firm* — Levine Bagade Han LLP

(57) ABSTRACT

Methods and devices described herein facilitate ablation patterns on the heart within a pericardial sac and without opening or deflating the lungs.

30 Claims, 34 Drawing Sheets

(56) References Cited

U.S. PATENT DOCUMENTS

| | | |
|---|---|---|
| 6,666,861 B1 | 12/2003 | Grabek |
| 6,811,551 B2 | 11/2004 | Dae et al. |
| 6,849,075 B2 | 2/2005 | Bertolero et al. |
| 6,918,908 B2 | 7/2005 | Bonner et al. |
| 6,923,806 B2 | 8/2005 | Hooven et al. |
| 9,173,705 B2 | 11/2015 | Whayne et al. |
| 2005/0192633 A1* | 9/2005 | Montpetit .......... A61B 17/0469 606/232 |
| 2008/0114355 A1 | 5/2008 | Whayne et al. |
| 2008/0208184 A1 | 8/2008 | Davies |
| 2009/0254078 A1 | 10/2009 | Just et al. |
| 2009/0326511 A1* | 12/2009 | Shivkumar ............ A61B 90/04 604/506 |
| 2011/0313286 A1 | 12/2011 | Whayne et al. |

* cited by examiner

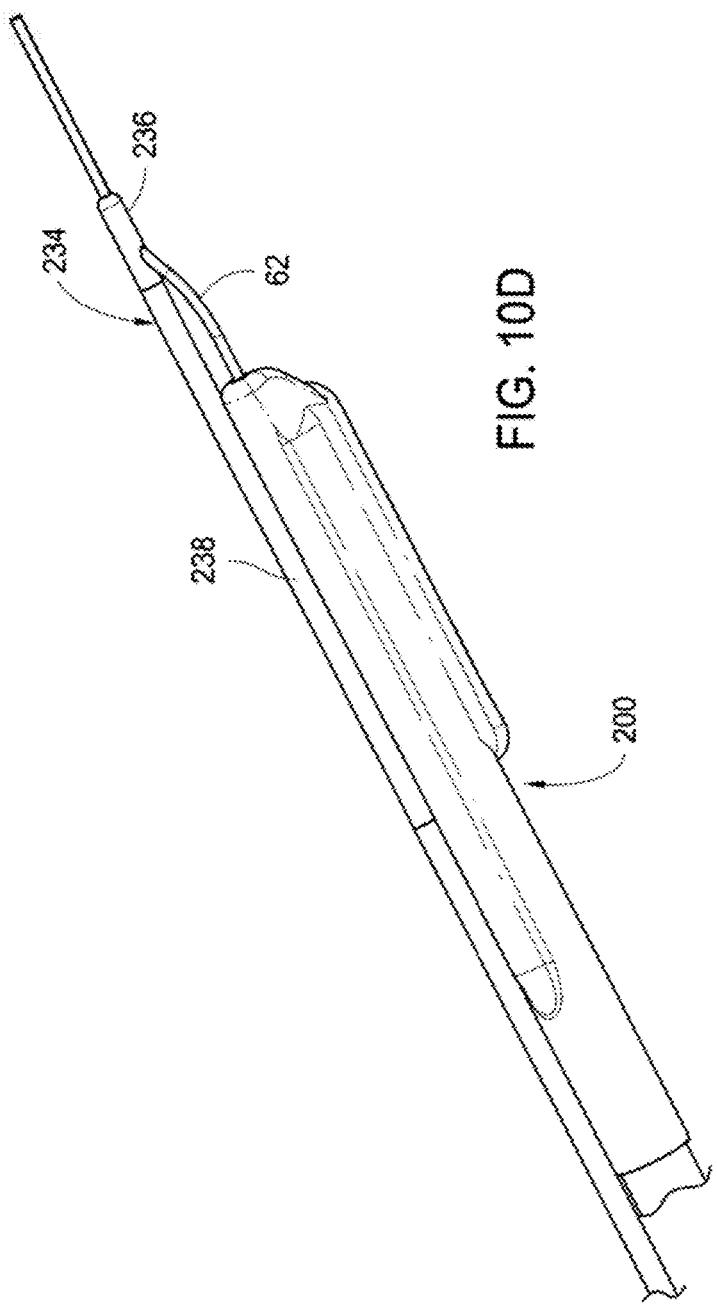
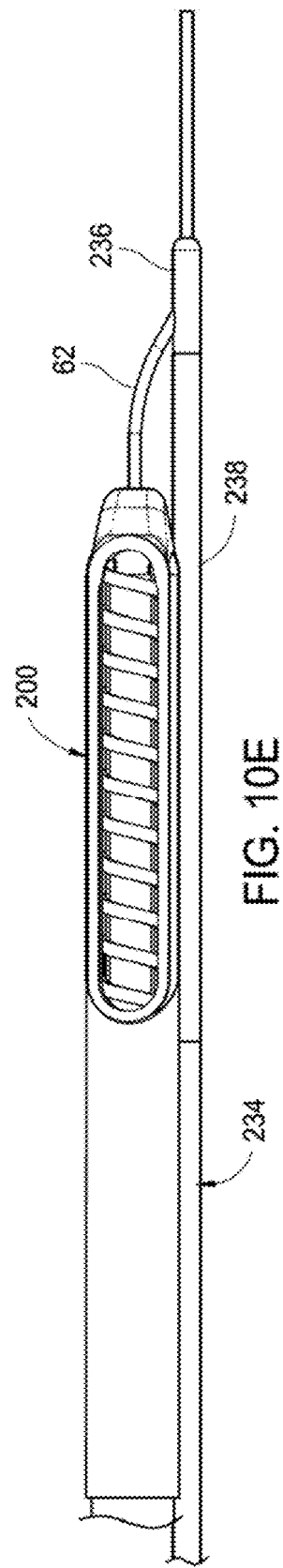

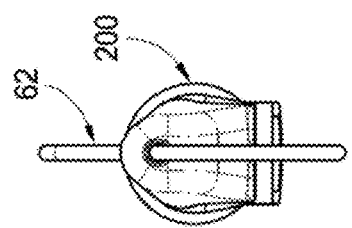
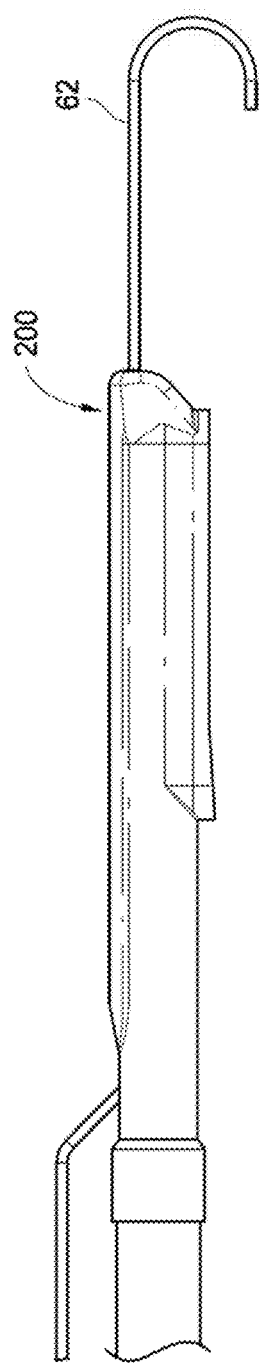
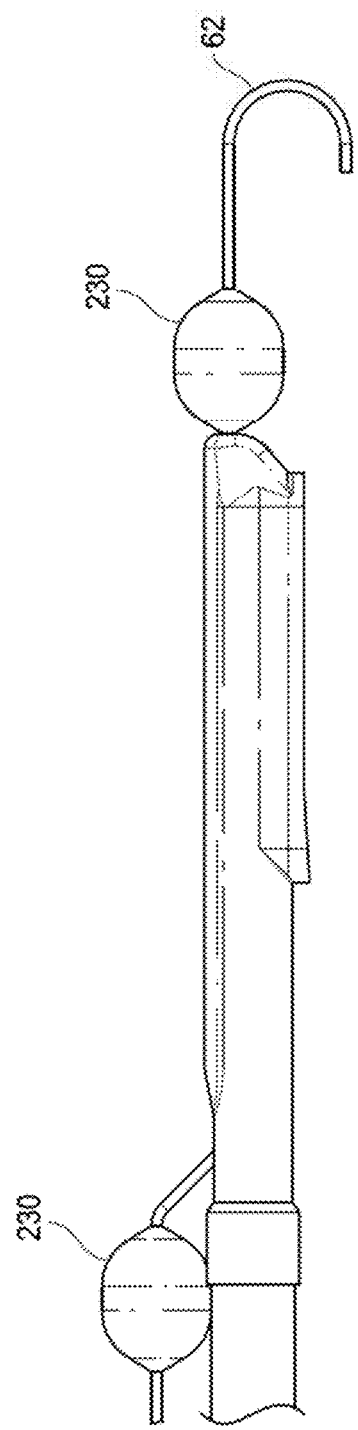
FIG. 12B
FIG. 12A
FIG. 12C

SUBXYPHOID EPICARDIAL ABLATION

RELATED APPLICATIONS

This application is a continuation of U.S. patent application Ser. No. 13/107,747 filed, May 13, 2011, which is a non-provisional of U.S. Provisional Applications 61/334,499 filed May 13, 2010 and 61/334,519 filed May 13, 2010, the entirety of each of which is incorporated by reference herein.

BACKGROUND OF THE INVENTION

Methods and devices for access devices to allow improved manipulation of organs and/or instruments within the body by creating working spaces within the body and adjacent to a target site. The methods and devices can be used in various parts of the body. One particular application includes the use of the access devices and methods to advanced devices to a surface of the heart to create atrial lesion patterns one or more atrial surfaces of the heart.

Scope based surgical tools (e.g., elongated cannula/tubular devices that allow viewing of internal body tissues) provide surgeons with an ability to view a surgical site through a lens/fiber optic/camera of the scope and also provide an ability to access the surgical site through a working channel of the tool. In some cases, a scope permits the surgeon to access internal body tissue by passing the scope through a small diameter opening, port, or trocar placed in a surface of the body.

In many surgical procedures, the surgeon must also dissect tissue to gain access to the intended target site. For example, U.S. Pat. No. 5,205,816 (the entirety of which is incorporated by reference) teaches a simple blunt dissector having a cannulated single lumen device with a mandrel inserted into the device for carrying a simple textured cloth that provides a textured surface. However, such basic devices are used in addition to the scopes that are used for such minimally invasive procedures. The additional blunt dissector requires an additional entry port or must be exchanged with other tools that are advanced through the entry site. In addition, a physician must manipulate a scope as well as the blunt dissection device.

Increasingly, scopes are being adapted to assist in the dissection of tissue to eliminate the need for an additional dissection device. Clearly, doing so reduces the number of devices that a physician must manipulate in the surgical area as well as the number of devices that are advanced through the body opening/port/incision. Many conventional devices rely upon balloon-type structures for dissection of tissue via expansion of the balloon or close-ended obturator-type structures that dissect via dilation via insertion of the closed end.

For example, U.S. Pat. No. 6,989,018 to Fogarty et al. (the entirety of which is incorporated by reference herein) discloses a balloon dissection apparatus having an elongate balloon that performs the tissue dissection. However, because this dissection relies upon somewhat uncontrollable expansion of the balloon (as the internal balloon pressure increases), the physician typically has less control over the amount of tissue dissection as compared to using a non-expanding structure to physically dissect tissue.

While obturator type devices avoid the problems with somewhat unpredictable dissection via balloon expansion, such devices are still not optimal. For example, U.S. Pat. Nos. 6,592,604; 6,752,756; and 7,001,404 (the entirety of each patent incorporated by reference herein) describe tissue dissection devices having with closed ends (where such ends act as obturators). The closed ends are generally translucent to allow for visualization therethrough. Yet, dissection of tissue occurs via dilation of the tissue using the closed end. U.S. Pat. No. 7,300,448 (the entirety of which is incorporated by reference herein) discloses a combination balloon dissector having an obturator associated with the balloon dissector assembly.

In any event, the balloon dissection or dissection via obturator dilation as described above do not provide the physician with the ability to tease or loosen adjoining tissue for a more controlled dissection of tissue.

Another drawback with conventional devices is their failure to accommodate removal of debris that is generated by the tissue dissection process. Such debris interferes with visualization through the scope. For example, during tissue dissection the resultant blood often smears the visualization scope. Alternatively, tissue debris (e.g., fatty deposits, etc.) present at the surgical site adheres to the visualization element. Even bodily fluids and the inherent body temperature can combine to produce condensation over the visualization scope. Often, a separate irrigation source must flush the distal end of the scope to maintain proper visualization. For example, U.S. Pat. No. 6,176,825 (incorporated by reference herein) discloses a cannula based irrigation system having a separate moveable irrigation member within the device.

Without the ability to irrigate the scope, a physician will be forced to repeatedly remove the scope from the surgical site and body for cleaning. Removal and cleaning of the scope increases the length and therefore the risk associated with the surgical procedure. Moreover, apart from the debris, in the obturator-type devices described above, the closed transparent end of the device often causes a distorted view of the working area.

Atrial fibrillation surgery is one example of a surgical procedure that relies upon dissection of tissue to access the target tissue site. To access the fibrillation surgery site, a physician typically dissects through tissue under direct visualization using an endoscope. Preferably, once the physician reaches the target site, the physician will establish a working channel or access path to the target site for the advancement of various surgical devices.

Accordingly, there remains a need for improved access devices that are configured to aid a physician during dissection of various tissues to access a target tissue site by providing the ability to gently dissect as well as establish space required to perform the intended procedure. The improved methods and devices described herein offer improved access to tissue regions within the body, especially those organs in the thoracic cavity. However, the devices and methods have applicability to any region in the body apart from the thoracic cavity.

For convenience, the following disclosure makes reference an endoscope as the scope based device. However, the inventive devices and methods described herein specifically include the use of any number of scope based devices generally similar to an endoscope; for example, any type of rigid or flexible tube with a light delivery system and a visualization source that transmits an image to the viewer, and (optionally) a working channel or lumen that permits delivery of an additional device through the scope.

SUMMARY OF THE INVENTION

Aspects of the invention are directed to devices and methods for less invasive treatment of atrial fibrillation. The subject coagulation probes for ablation and/or coagulation integrate suction to the coagulation mechanism so as to ensure consistent and intimate tissue contact directly between the coagulation mechanism and soft tissue. The subject coagulation probes may also have features allowing for advancement or positioning of the probes using a track-member as described below.

Increased tissue contact relative to that which can be achieved with known devices is capable of reversing convective cooling effects effect noted above by evoking a compression of the tissue that shortens the wall thickness (e.g., of the atria), ensuring consistent contact throughout the length of the electrode(s), and increasing the efficiency of thermal conduction from the epicardium to the endocardium. As such a more consistent and reliable lesion is created.

The method includes creating a lesion on a surface of a heart in a body of a patient during a minimally procedure. In one variation, the method comprises creating a minimally invasive incision to access a chest cavity of the patient; creating an opening in a pericardium of the patient and positioning a dilation device into the pericardial space; creating a path within the pericardial space by expanding the dilation device, deflating the dilation device, and then repositioning and re-expanding the dilation device; advancing a treatment device through the path to position the treatment device against a surface of the heart; and creating the lesion on the surface of the heart using the treatment device.

Variations of the method include advancing a guide wire into the pericardial space and where positioning the dilation device into the pericardial space comprises advancing the dilation device over the guidewire. The term guidewire, unless specifically stated otherwise, can mean any wire, catheter, or guide type device.

The method can further include withdrawing the dilation device from the guidewire, and where advancing the treatment device comprises advancing the treatment device over the guidewire.

Expanding the balloon can occur during creating of the lesion to separate an anatomical structure from the heart surface. For example, the phrenic nerve or esophagus can be separated or spaced from target tissue to minimize unintentional damage to such structures. Alternatively, or in combination, the method can include cooling tissue using the dilation device before, during or after creating of the lesion.

Furthermore, fluid can be delivered to the pericardial space to provide drugs or other substances to the treated area, or to maintain a fluid layer between the heart surface and the pericardium. Alternatively, the fluid layer can maintain be maintained to cool the surface of the heart or to provide visualization of the heart tissue by advancing a visualization device into the fluid layer.

In an additional variation, the method can further include drawing a vacuum in the vacuum source to cause a drop in pressure in both the vacuum lumen and the opening, whereupon placing the opening against the soft tissue creates a seal against the soft tissue to cause the fluid perfusion lumen to drop in pressure resulting in fluid flow from the fluid source through the fluid perfusion lumen across the opening and through the vacuum lumen, where when uncovered the opening prevents the perfusion lumen from reducing in pressure and preventing fluid flow.

The present disclosure also includes a surgical device for creating a linear and/or curvilinear coagulation lesion in a soft tissue of an organ. One variation of the device includes a body having a housing at a distal end and an expandable member; an energy transfer element located within the housing and having an elongate exposed portion at an opening in the housing such that the exposed portion of the energy transfer element is capable of creating the linear and/or curvilinear coagulation lesion in the soft tissue; a first diagnostic element assembly positioned adjacent to a distal section of the energy transfer element and opposite to the expandable member such that expansion of the expandable member against a body structure directs the energy transfer element against the soft tissue. A variation of the surgical device includes at least one diagnostic electrode located on a flexible base member.

The present disclosure also includes methods of perfusing a pericardial space. In one example, the method includes advancing a perfusion device through an incision in a pericardium, where the perfusion device comprises a first lumen terminating at a first opening and at least a second lumen terminating at a second opening, where the first and second lumen are fluidly isolated from each other within the perfusion device, and where the first opening is located proximally along the perfusion device relative to the second opening; positioning the first opening within the pericardial space and adjacent to the incision in the pericardium; delivering fluid through the second opening such that the fluid enters the pericardial space; and evacuating fluid from the pericardial space through the first lumen.

The method can also include securing the perfusion device to the pericardium. For example one or more balloons or expandable members can be used to secure the device within the pericardial space or about the pericardium.

The method can also include inserting a visualization device into the pericardium, where delivering fluid through the second opening permits direct visualization within the pericardial space. Placement of the perfusion device can occur using one or more radiopaque markers to allow for positioning of the first or second openings under non-invasive imaging. Moreover, the perfusion device can also be placed using direct visual imaging via insertion of a scope type device within or near the pericardial space.

The present disclosure also includes a perfusion device for delivering fluid to a pericardial space. In one example, the perfusion device includes a flexible shaft comprising at a first lumen terminating at a first opening and a second lumen terminating at a second opening, where the first opening is proximally located along the shaft relative to the second opening; a radiopaque marker adjacent to the first opening to allow for placement of the first opening within a pericardium; at least one expandable member located proximally along the shaft relative to the first opening, when expanded causes the perfusion device to be temporarily secured within the pericardial space. Variations of the perfusion device include with a second balloon or expandable member. Alternatively, an expandable member is not required in which case the device can be secured to the pericardial space via temporary suturing, clamping or through a resistance fit between the shaft of the device and local anatomy.

The perfusion device can optionally be coupled to a vacuum source and to a fluid source.

The subject matter of this application may be incorporated with the subject matter in the following commonly assigned patents, publications, and/or applications: the entirety of each of which is hereby incorporated by reference.

Variations of the access device and procedures described herein include combinations of features of the various embodiments or combination of the embodiments themselves wherever possible.

BRIEF DESCRIPTION OF DRAWINGS

FIGS. 10A to 10F illustrate variations of a coagulation probe optionally configured with pacing and/or sensing capabilities as well as a coagulation element within a single probe.

FIG. 12A to 12C shows dilation members located on a guidewire that is coupled to a treatment device.

DETAILED DESCRIPTION

Methods and devices described herein provide for improved manipulation of organs and/or instruments within the body by creating working spaces within the body and adjacent to a target site. While the following disclosure discusses devices and methods for use in the thoracic cavity, such methods and devices can be applied to various body portions outside of the thoracic cavity. The methods and devices may allow for direct visualization along regions of anatomic structures not attainable with conventional approaches.

Furthermore, the methods and devices described herein may be used in conjunction with, or as an alternative to the conventional approaches described herein. For example, while some surgical approaches and procedures described herein rely on entry through the diaphragm of a patient to access a regions of the thoracic cavity, the surgical approaches and procedures can be combined with various other access methods.

Figure 1:
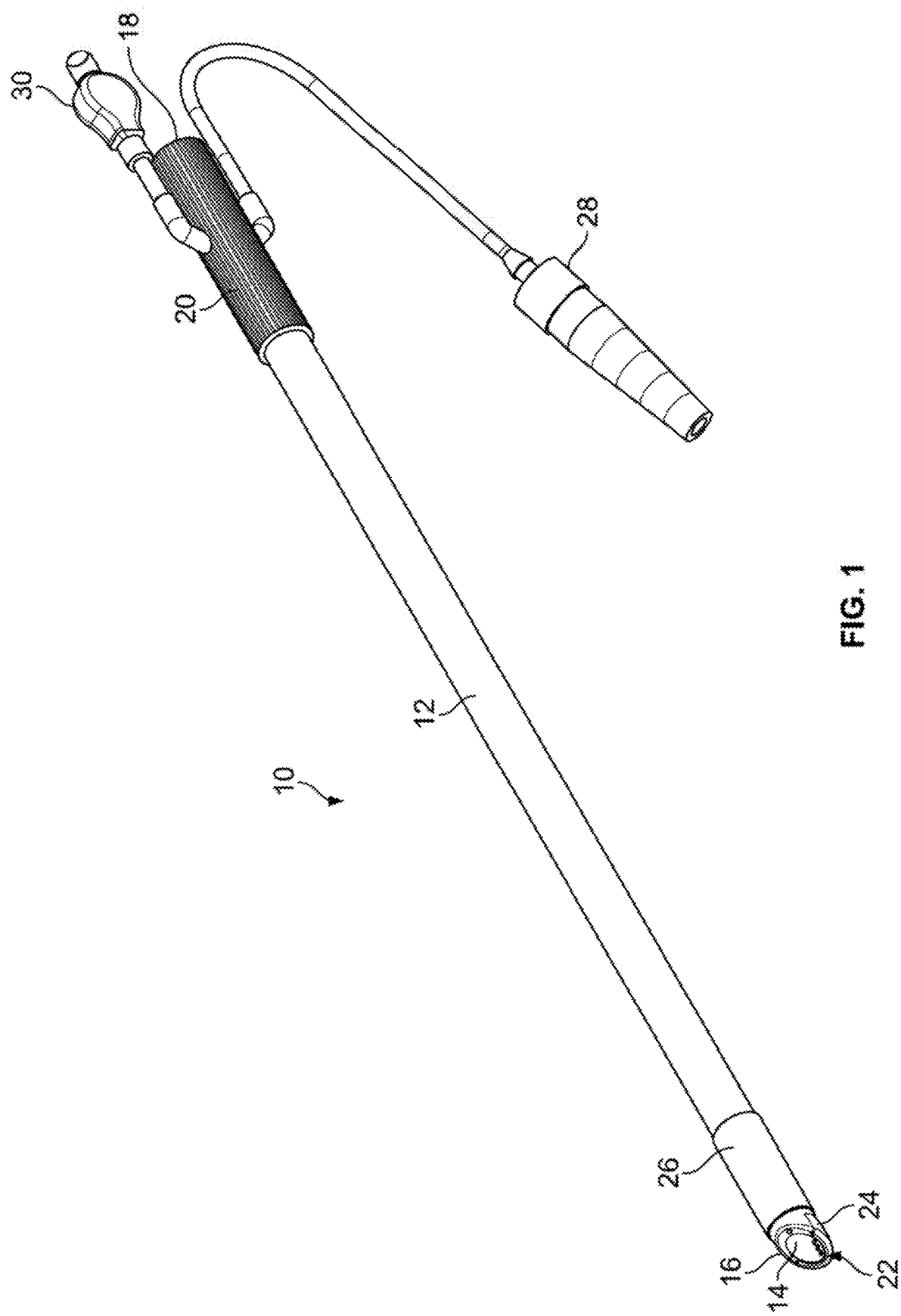
FIG. 1 shows one example of a tissue dissection access device configured to dissect tissue using a number of different tissue dissection modalities.

FIG. 1 shows one example of a tissue dissection access device 10 configured to dissect tissue using a number of different tissue dissection modalities. As described above, devices according to the present invention that provide a number of dissection modalities, e.g., frictional dissection, wedge-type dissection, and dilation type dissection, provides a physician with a number of options to access a target site during a minimally invasive procedure.

FIG. 1 shows a device with several tissue section modalities. However, certain variations of devices within the scope of this invention can have any sub-combination of tissue dissection modalities.

Turning now to the illustrated variation, the first dissection modality comprises a dilation wedge tip 22 or beveled tip located at the distal end of the cannula 12. The wedge shaped tip provides a mechanical wedge dissection modality as the tip 22 can be inserted into small openings in tissue and where advancement of the tip 22 mechanically dilates the opening.

The second dissection mode comprises a dissection surface 24 located on a side of the dilation wedge 22. The dissection surface 24 provides a frictional or abrasion dissection modality as the physician is able to apply the tip to a tissue surface and gently dissect the tissue apart by relying upon the increased friction between the dissection surface 24 and the tissue. The dissection surface 24 can dissect tissue via axial movement relative to the tissue, by rotational movement, or a combination thereof. In certain variations, the dissection surface 24 can be configured to dissect tissue when moved in a single direction (as discussed below). For example, the dissection surface 24 can be configured to catch tissue as it is pulled in a proximal direction. This allows distal advancement without resistance. In any case, as the surface 24 moves against tissue, the increased friction of the surface 24 catches on tissue to gently separate fibers of soft tissue. Although the variations shown herein depict the dissection surface on an end of the dilation wedge 22, the dissection surface 24 can be located on the cannula surface or even on a balloon dilation surface.

The third dissection mode comprises an expandable dilation balloon member 26 located on a surface of the cannula 12. The dilation balloon member can be a distensible or non-distensible balloon. Generally, the dilation balloon member 26 can be used to create a temporary cavity or to separate tissue to a greater degree than a diameter of the cannula 12. Any number of expandable members can be used in place of a balloon (e.g., a mechanical basket, axially aligned flexible strands, an expandable helical wrapped ribbon or wire, etc.)

FIG. 1 also shows another feature of certain devices that provides a physician with unobstructed access to tissue sites that are exposed by tissue dissection. As shown in FIG. 1, the device 10 includes a cannula 12 having a working channel 14 extending therethrough and terminating at a distal opening 16. In certain devices the distal opening 16 is in-line with an axis of the working channel 14. This feature provides an ability to extend a medical device through the working channel 14 and directly into or adjacent the tissue being dissected. Such a feature is very beneficial when using the working channel to visualize tissue being or using the working channel to advance a device therethrough to treat a tissue site that is exposed by dissected tissue.

Accordingly, a physician can advance any such medical device from a proximal end 18 of the device 10 (as shown the device has an optional handle portion 20 on a proximal end) through the distal opening 16 and move the medical device relative to the distal opening 10 in alignment with an axis of the working channel 14 of the access device 10. The handle can be configured to provide a textured surface to allow a physician to grip and manipulate the device.

The cannula shaft (or the portion of the cannula 12 between the wedge tip 22 and the proximal portion 18 or handle portion 20) can be constructed to have a number of different configurations. For example, the cannula shaft can be flexible such that it can be deflected from an axis of the distal opening 16. However, the cannula shaft shall have a column strength that allows a physician to push or advance the device into tissue or between organs. In some cases, the flexibility of the shaft allows flexion when medical devices are placed therethrough. This can reduce forces placed on the target tissue. Alternatively, use of rigid medical devices placed within the working channel 14 can change the flexibility of the shaft to increase the ease by which the device 10 is remotely manipulated within the body. The cannula 12 can be fabricated from any variety of medical grade materials. In one variation, the cannula is constructed from either silicone or C-Flex.

The device 10 also includes any number of fittings to couple the device to a fluid or vacuum source. As shown, the device 10 includes a first fluid connector 28. In this variation, the fluid connector 28 can be connected to a vacuum or fluid source to remove fluids from the working channel 14 of the device or deliver fluids to the working channel 14. The fluid connector 28 can also be connected to a vacuum source and fluid source simultaneously via the use of a two way valve or similar type of flow diverters (e.g., a two way stop cock). In those variations of the device 10 including an expandable dilation member 26, a separate connector 30 can be provided to couple the dilation member 26 to a source of pressure (either air or fluid).

Figure 2A:
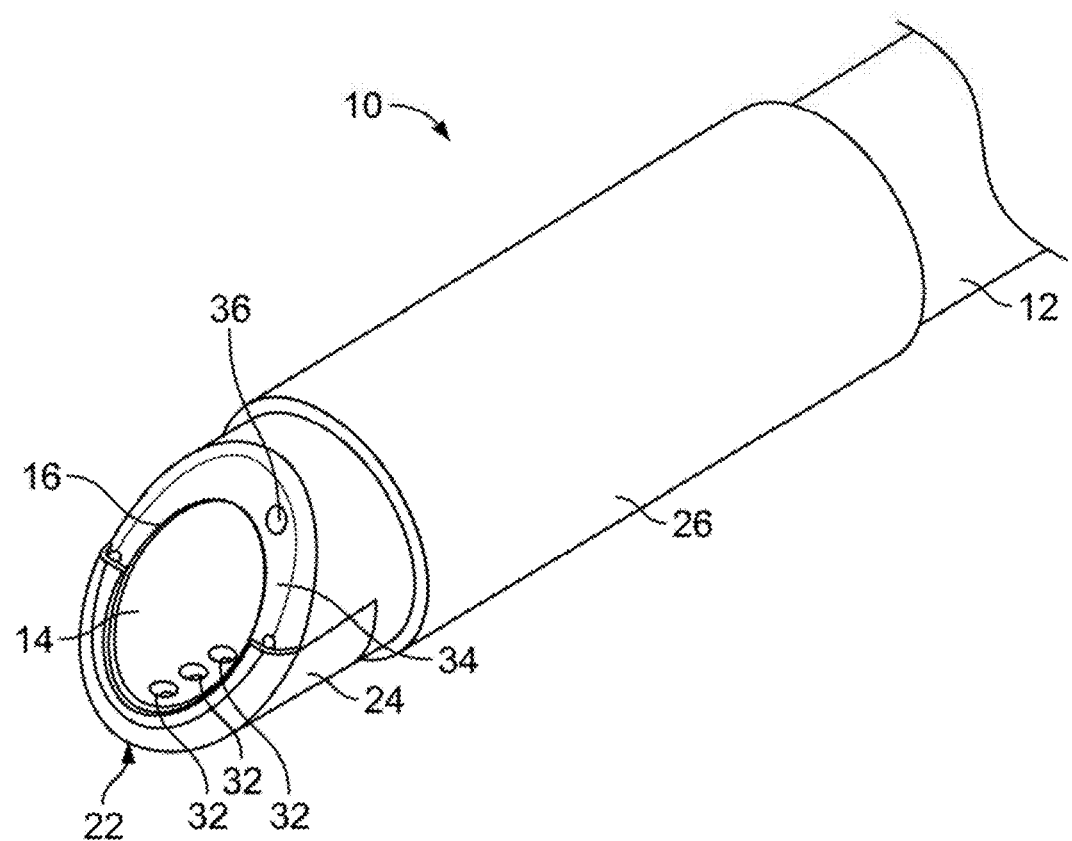
FIG. 2A depicts a magnified view of a working end of the device of FIG. 1.

FIG. 2A depicts a magnified view of a working end of the device 10 of FIG. 1. As shown, the working channel 14 also includes a plurality of fluid ports 32 located therein. As noted above, the fluid ports 32 are coupled to a fluid source for delivering a fluid to irrigate the target tissue or a medical device located within the working channel 14. The fluid ports 32 also allow a physician to remove debris or fluid from the working channel 14.

In the variation of the device 10 shown, there are a number of fluid ports 32. Additional variations of the device include a single fluid port 32. However, multiple fluid ports 32 provide an advantage to generate a larger area of fluid flow within the working channel 14. Such a feature improves the ability of the device 10 to clean a medical device located therein by providing a greater area to deliver or remove fluid. In the variation shown, the fluid ports 32 are located within the bevel of the dilation wedge 22 and are placed in alignment along an axis of the working channel 14. However, the fluid ports 32 can also be arranged in a non-aligned manner or a random pattern. In addition, variations of the device 10 include fluid ports arranged on an exterior of the cannula 12 or proximal to the dilation wedge tip 12 within the working channel 14.

FIG. 2A also depicts additional aspects of the device 10. As shown, the dilation wedge 22 comprises a transition surface 34 along the distal opening 16 that provides a smooth transition to the outer surface of the cannula 12. This feature aids in dilating tissue from a small opening to a larger opening that is the size of the outer diameter of the cannula 12. FIG. 2A shows another optional feature of a visualization element 36 located on a front face of the device 10. Such elements can include a fiber optic scope or line as well as a CCD camera or any such visualization component as commonly known and used with various medical scopes.

In addition, although the working channel 14 and distal opening 16 are frequently depicted as having a circular cross section, variations of the device contemplate the working channel 14 and distal opening 16 to have non-cylindrical openings. For example, the cross-sectional profile can include oval or rectangular shapes where a height and width of the channel are not equal. The benefit of such configurations is that multiple devices can be advanced parallel within the working channel.

Figure 2B:
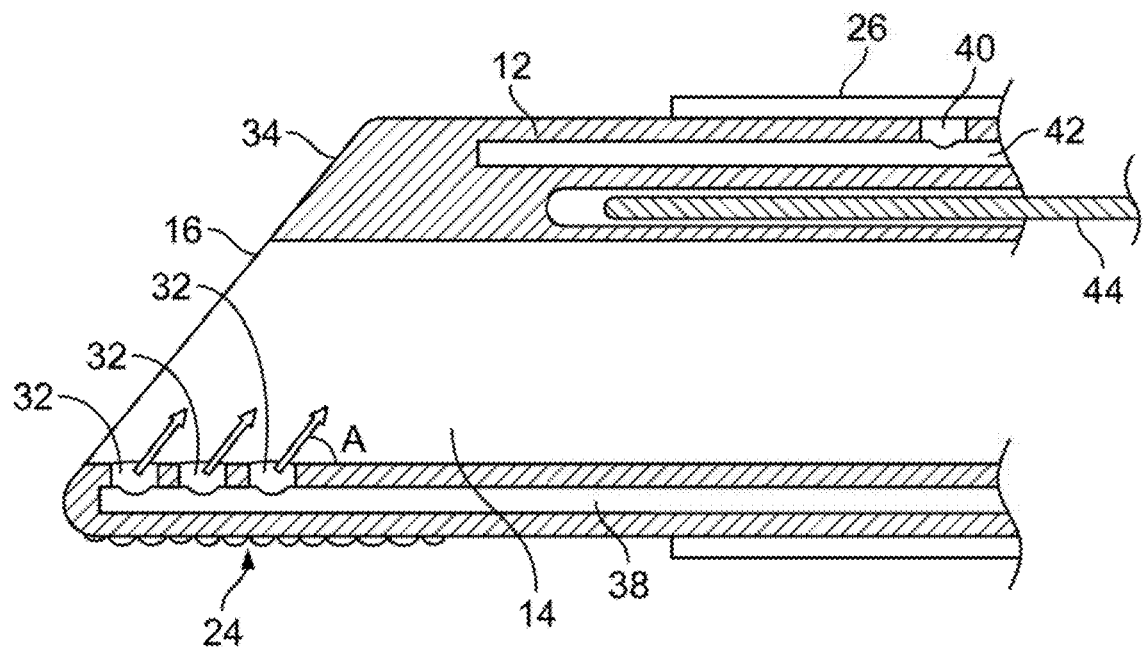
FIG. 2B shows a partial cross sectional view of a variation of a working end of a tissue dissection access device.

FIG. 2B shows a partial cross sectional view of a variation of a working end of a device 10 according to the present invention. As shown, the device 10 includes a plurality of fluid lumens 38, 42 coupled to respective fluid ports 32, 40. As noted above, fluid ports 32 can be placed in fluid communication with the working channel 14 to irrigate and remove fluids to or from the channel 14 for the clearing of debris from medical devices advanced within the working channel 14. One or more fluid ports 40 also can be placed within the expandable dilation member 26 for pressurization of the member 26 to dissect or separate tissue. In certain variations, the fluid ports 32 located within the working channel 14 are angled or directed towards a proximal end of the device 10 (e.g., such that an axis of the port 32 forms an angle A that is less than 90 degrees. Directing the ports 32 in such a manner permits fluid to be delivered to the face of any device advanced within the working channel.

FIG. 2B also shows an optional support member 44 located within a wall of the cannula 12. The support member can be rigid or shapeable. A malleable or shapeable support 44 may be incorporated into a portion or an entirety of the cannula 12 to allow shaping the member into a desired configuration. The shape is selected to improve the ability of the device to direct the scope and instruments towards the desired site within the body (e.g., a region of the surface of the heart, or other anatomic structure). The support 44 can be placed in a support lumen such that the support 44 is slidable within the support lumen of the cannula 12. The support 44 can be removable from the cannula 12. In certain variations, it may be desirable to minimize a wall thickness of the cannula 12 to maximize the working channel 14 diameter and minimize the outer diameter of the cannula 12. In such a case, the device will not be constructed to have a support member 44 or will not have the visualization element 36 shown in FIG. 2A.

FIGS. 3A to 3D show variations of different dissecting surfaces 24 for use with devices as described herein. In some variations a device can be equipped with more than one type of dissecting surface 24. Moreover, a dissecting surface 24 can be placed on any portion of the device (including the expandable dilation member 26). Although the figures illustrate the dissecting surfaces 24 on the bottom edge of the cannula 12, the dissecting surfaces can extend over a full or partial perimeter of the cannula surface 12.

Figure 3A:
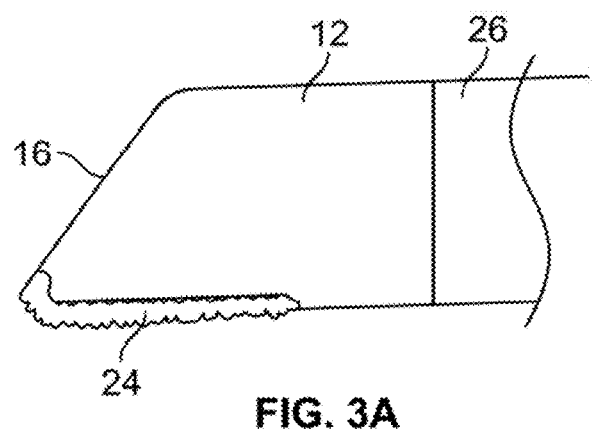
FIGS. 3A to 3D show variations of different dissecting surfaces for use with devices as described herein.

FIG. 3A shows a variation of a dissecting surface 24 that comprises a layer of material, such as a polymeric layer, a layer of cloth, or other surgical material that is textured and can be used to abraid tissue for dissection. In an additional variation, the material can comprise an absorbable surgical sponge material, such as gauze or other woven cotton. Alternatively, the material can be comprised of a polymeric material that is inserted into or onto the cannula 12 where the polymeric material comprises a sufficiently high coefficient of friction that the nature of rubbing the material against tissue results in abrasion and dissection of the tissue. The texture of the material abrades the tissue being dissected so that the dissection can be performed in either a distal or proximal motion of the cannula 12.

The cannula 12 can have a relief section removed for insertion of the material 24. In alternate variations, the material can be affixed to an exterior of the device. In certain variations, the material is non-absorbent and retains texture and stiffness as it encounters body tissue and fluids. The material can be glued onto the cannula 12 or the cannula 12 can have a textured or sharp surface to retain the material.

Figure 3B:
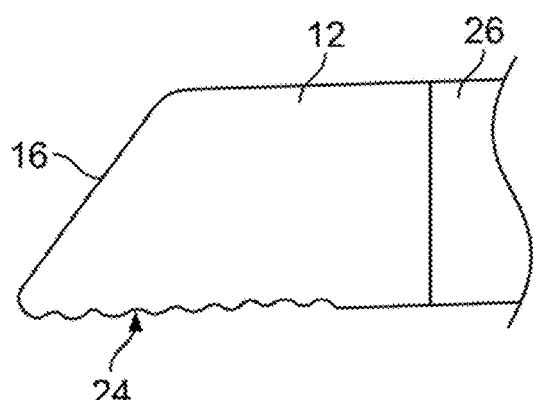

FIG. 3B shows another variation of a dissection surface 24. In this example, the dissection surface 24 is formed directly into the surface of the cannula 12 via a mechanical or chemical process. For example, the cannula 12 can be grounded, etched, swaged, bead-blasted, heat formed, etc. Alternatively, the textured dissection surface 24 could be formed in a mold such that the dissection surface 24 is directly molded onto the cannula 12.

Figure 3C:
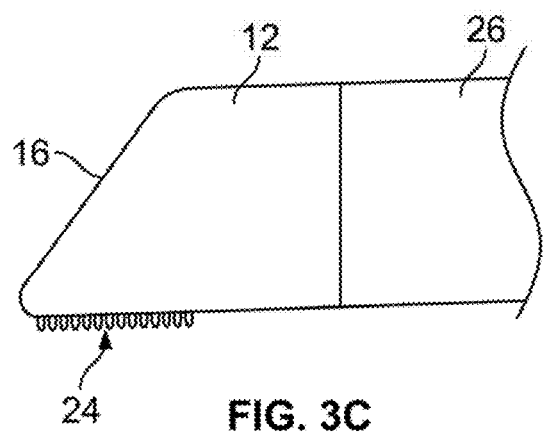

FIG. 3C shows another variation of a dissection surface 24 formed from a plurality of surfaces that extend from a surface of the cannula 12. For example, the surface 24 can be formed from granules deposited on the cannula 12 to form a sand-paper like coating. Alternatively, the surface 24 can comprise flexible extensions that engage and grip tissue when moved across the tissue.

Figure 3D:
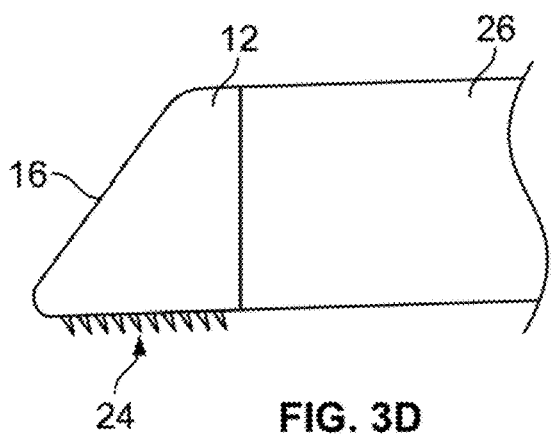

FIG. 3D shows yet another variation of a dissecting surface 24. In this variation, the dissecting surface 24 comprises a directional dissecting surface 24 as shown by the saw-tooth configuration. The dissecting surface 24 generally does not engage the tissue when moved in a first direction (in this case a distal direction) but engages tissue when moved in a second direction (in this case a proximal direction).

Figure 4A:
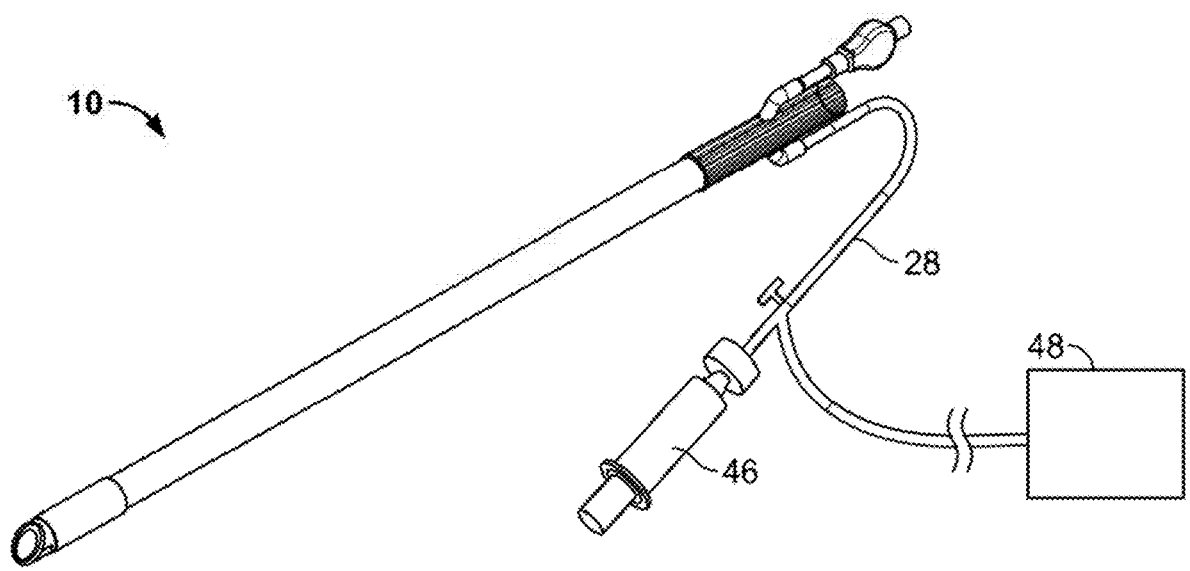
FIG. 4A illustrates a variation of a tissue dissecting device coupled to a syringe and vacuum source.

FIG. 4A illustrates a variation of a tissue dissecting device 10 coupled to a syringe 46 via a connector 28. Optionally, the device 10 can be simultaneously coupled to a vacuum source 48 via a two way valve.

Figure 4B:
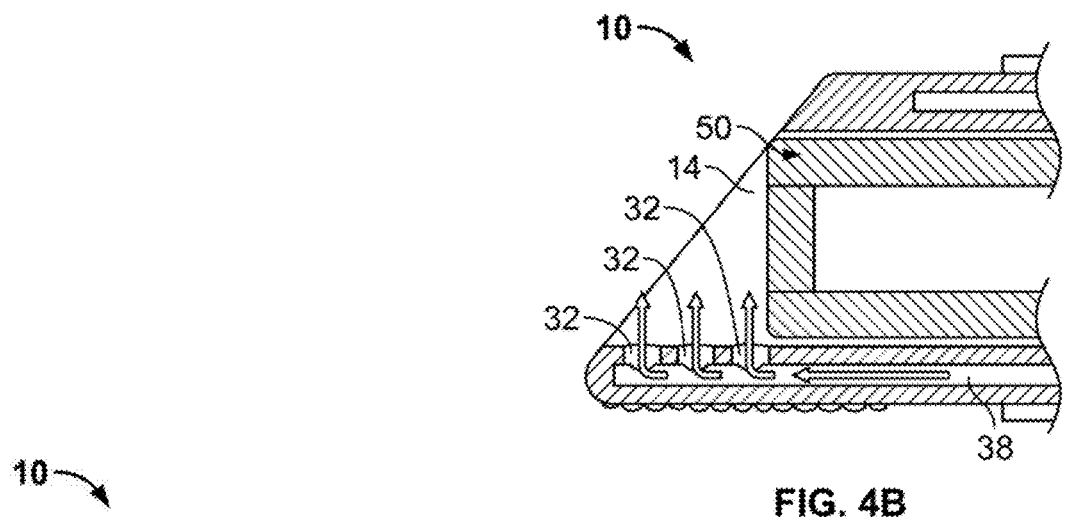
FIGS. 4B and 4C show irrigation and removal of fluids through ports in a working channel of a dissection access device.
Figure 4C:
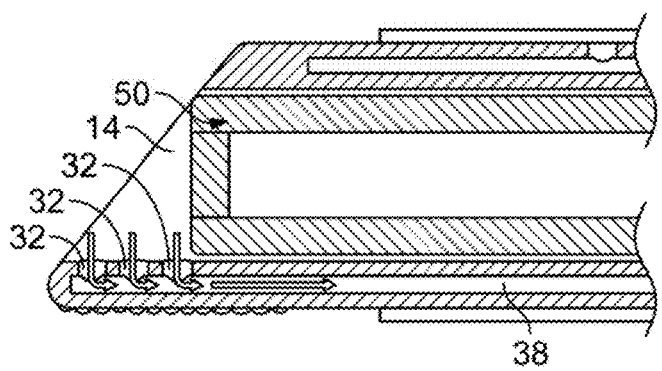

As described herein, the device 10 can accommodate a scope or medical device 50 such as an ablation device. Regardless of the medical device, as the tissue dissecting device 10 dissects tissue, various bodily debris and fluid often attach to the medical device advanced therethrough. In the case of a scope, the debris and fluid can prevent the scope from providing a clear image to the physician. In the case of energy delivery devices, debris attached to an energy transfer element can affect the energy transfer that should otherwise occur. As shown in FIG. 4B, injection of fluid through the fluid lumen 38 and fluid ports 32 into the working channel 14 bathes the end (or other area as appropriate) of the medical device 50 removing the debris and cleaning the device 50. FIG. 4C shows a state of the device 10 where suction is applied through the fluid lumen 38 to draw fluid and other debris into the fluid ports 32. Placement of the fluid ports 32 within the working channel 14.

Figure 5A:
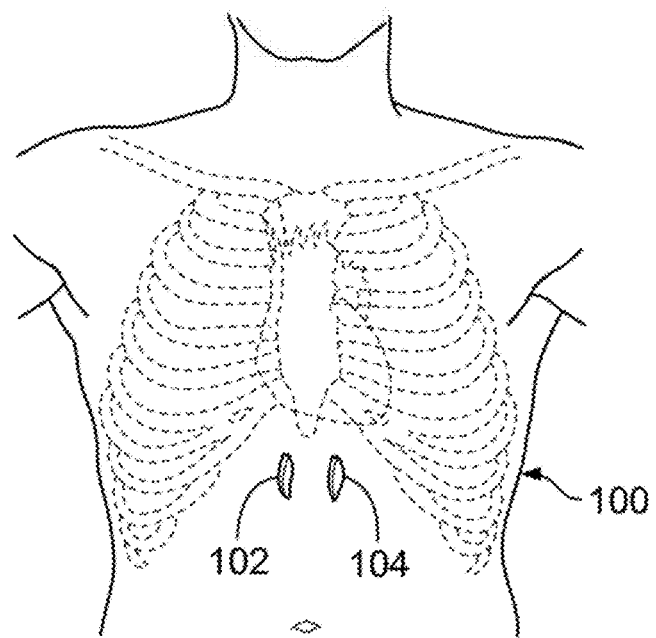
FIGS. 5A and 5B illustrate placement of a pair of devices within a body of a patient in an exemplary procedure to access a posterior region of the thoracic cavity.
Figure 5B:
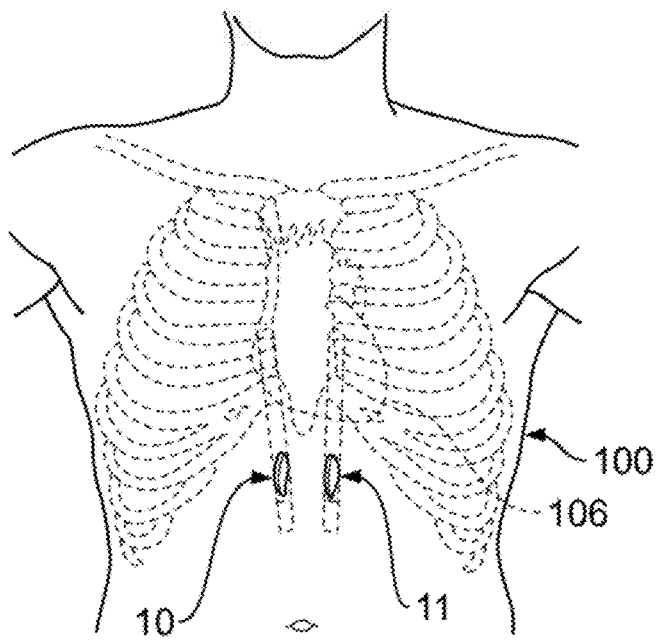

FIGS. 5A and 5B illustrate placement of a pair of devices 10 within a body 100 of a patient in an exemplary procedure. It is noted that the device 10 can be used in any part of the body and through any incision or port in a minimally invasive manner. However, the device 10 can also be used in open surgical procedures.

FIG. 5A illustrates creation of two incisions 102 104 in the body 100. In the illustrated example, the incisions are made in the abdomen of the patient so that the dissecting access devices 10, 11 can then pass through a diaphragm of the patient to a posterior side of the thoracic cavity (as shown in FIG. 5B).

Figure 6A:
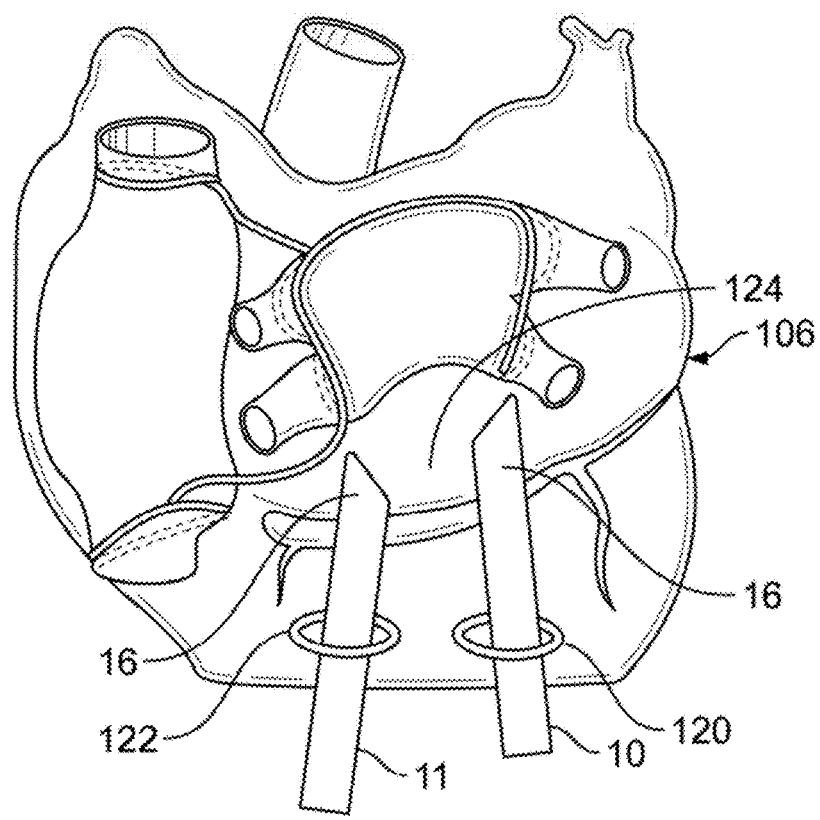
FIGS. 6A to 6Q show one exemplary use of the dissection access devices described herein to create bi-atrial lesion pattern on a posterior region of the heart.
Figure 6B:
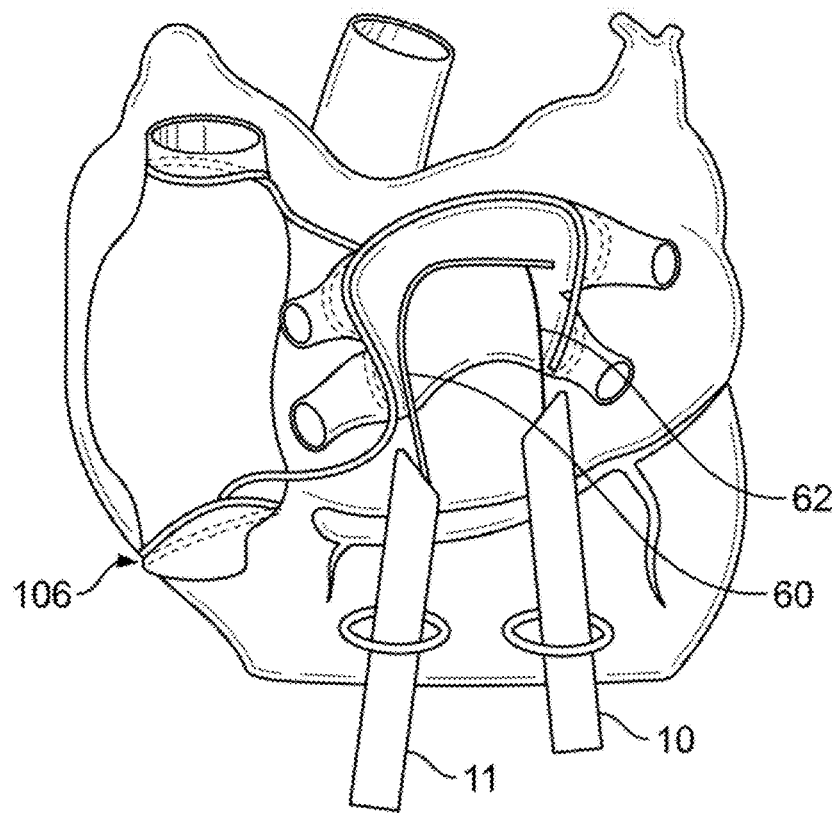
Figure 6C:
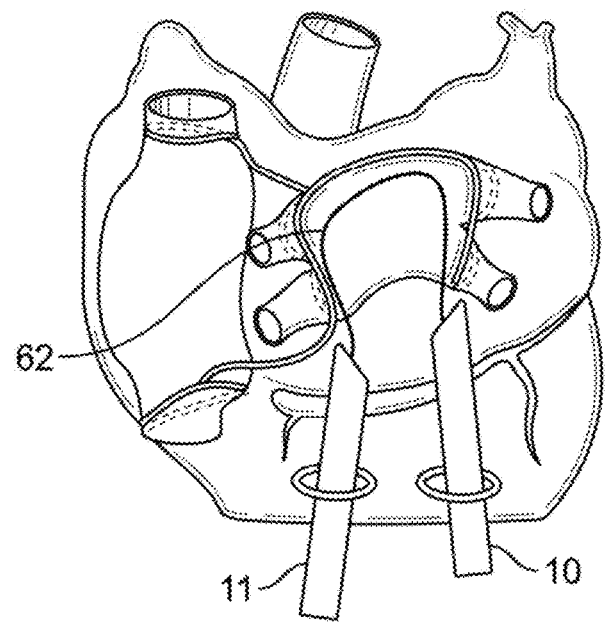
Figure 6D:
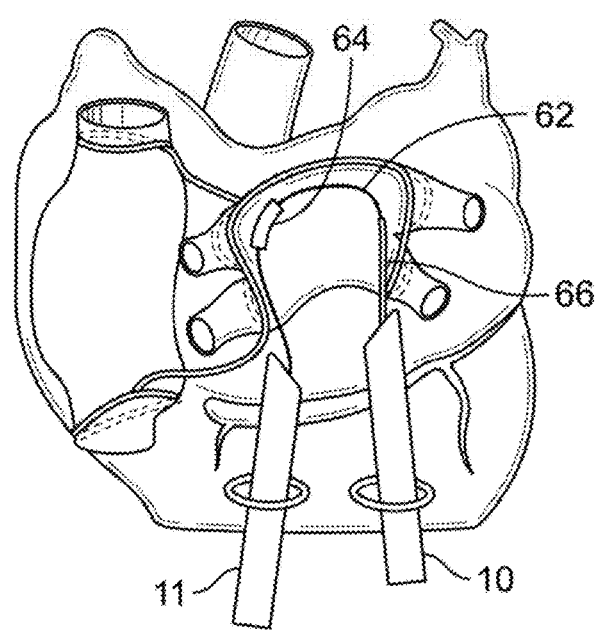
Figure 6E:
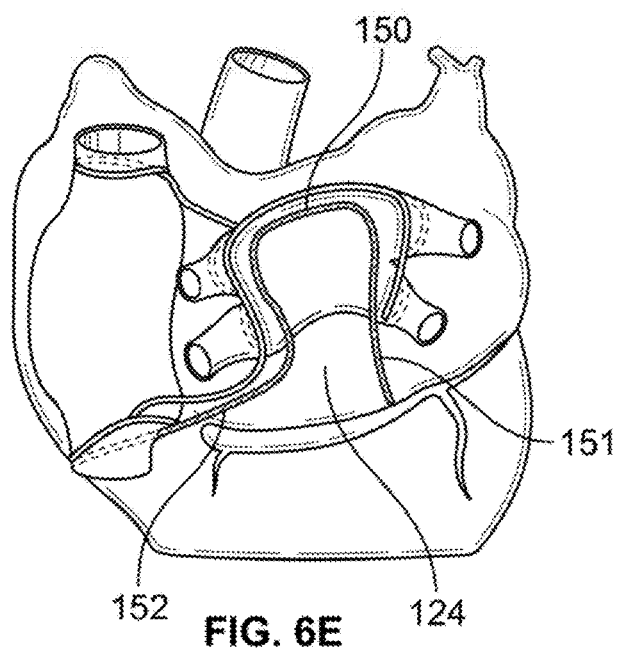
Figure 6F:
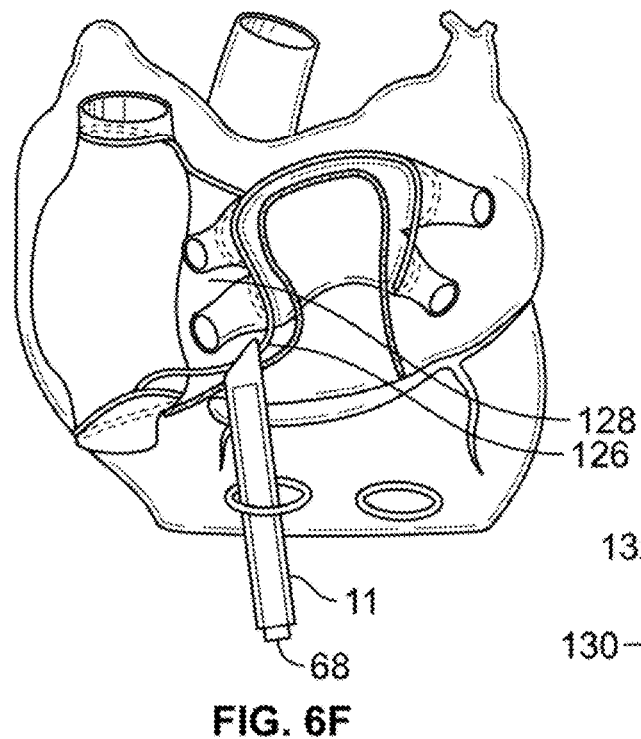
Figure 6G:
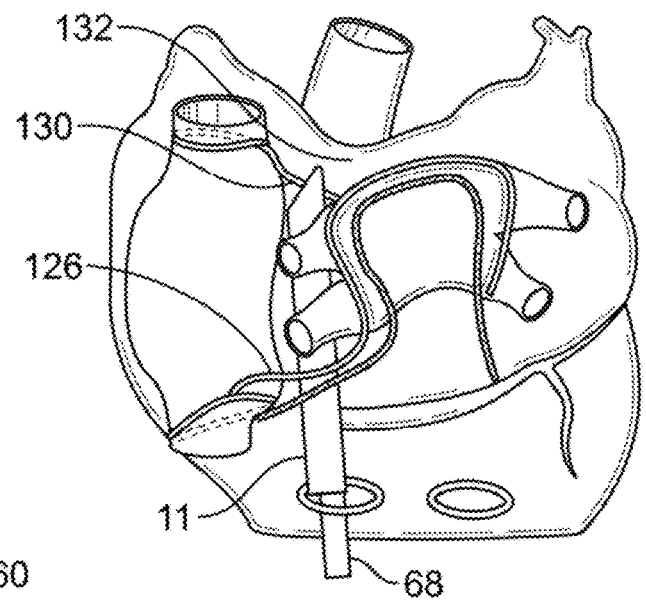
Figure 6H:
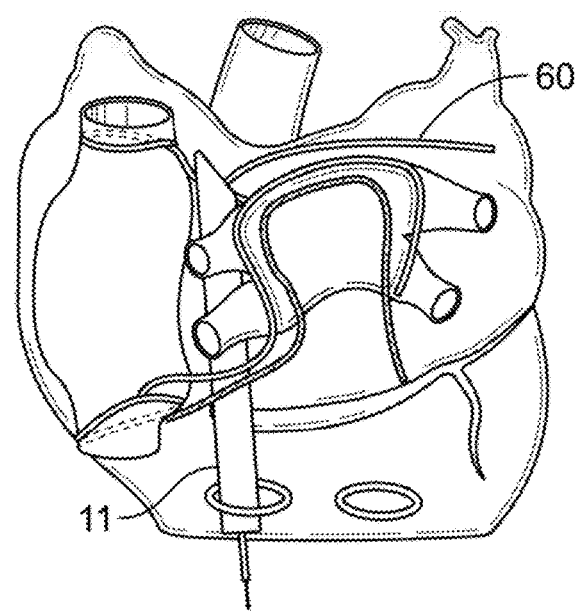
Figure 6I:
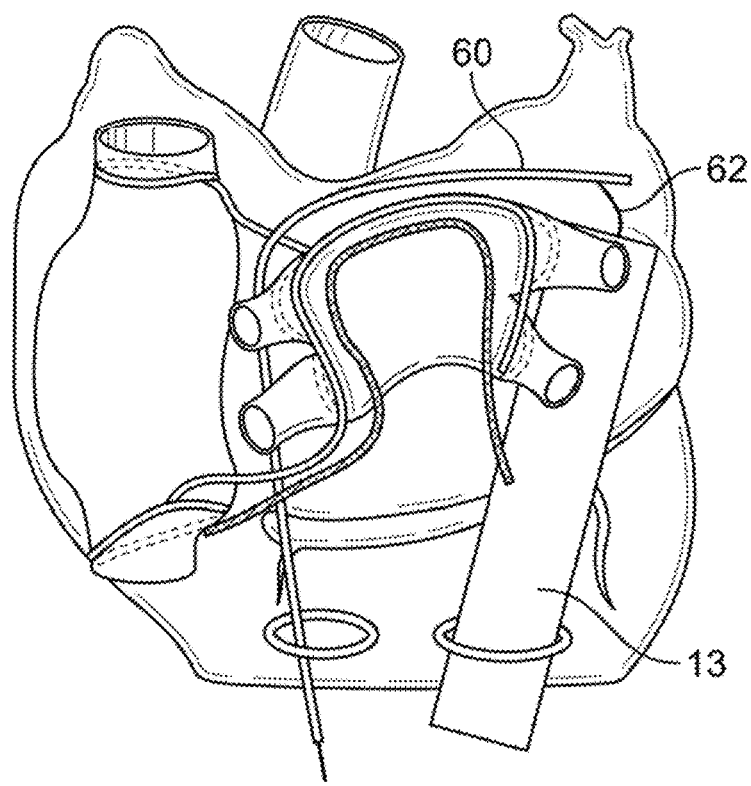
Figure 6J:
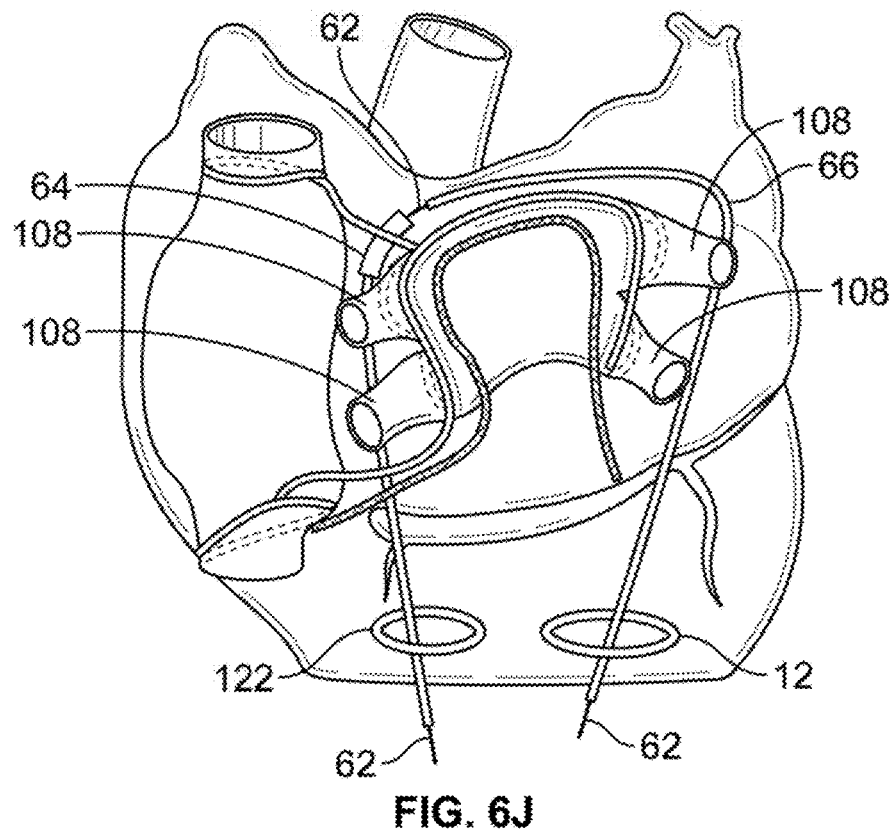
Figures 6K, 6L, 6M:
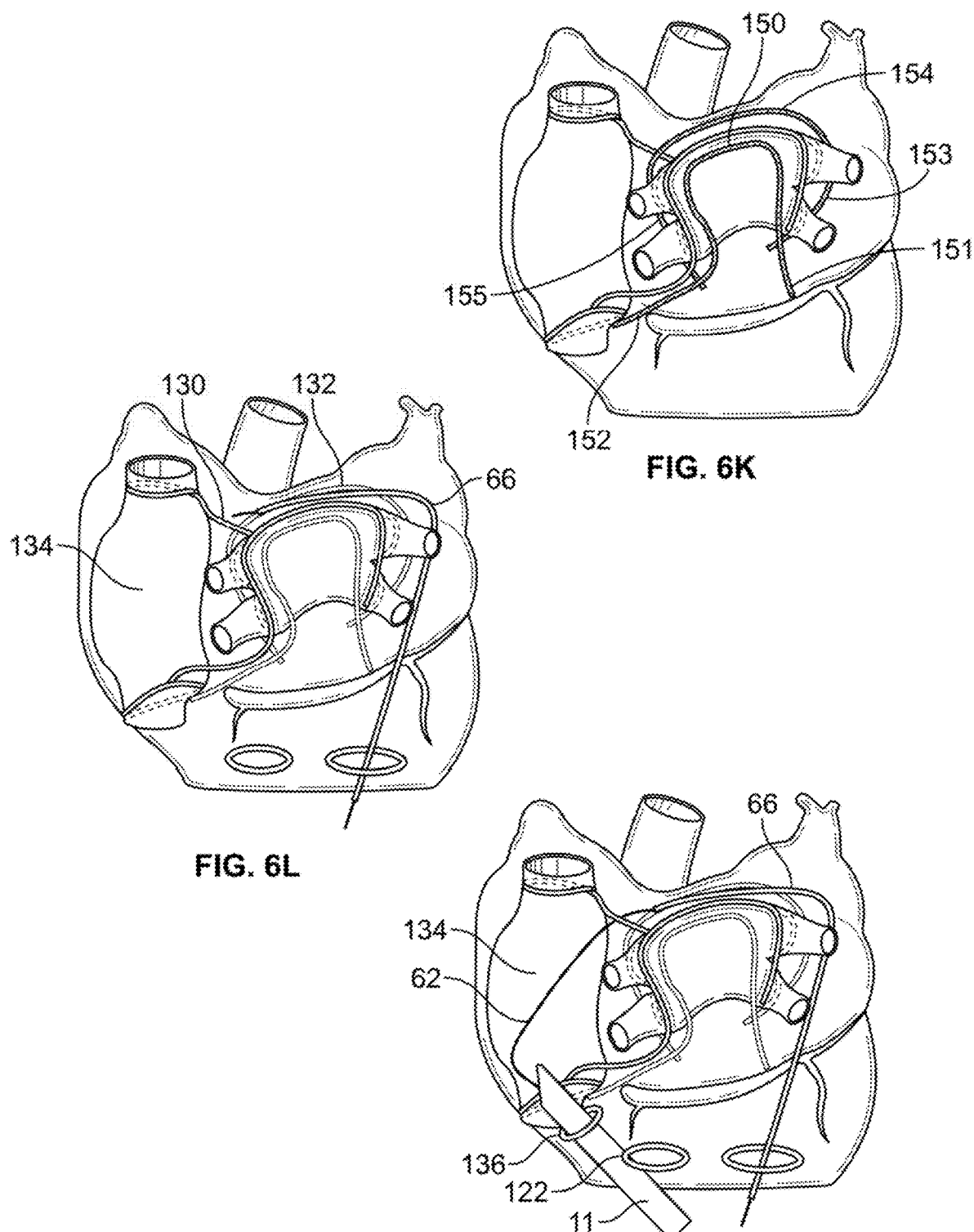
Figure 6N:
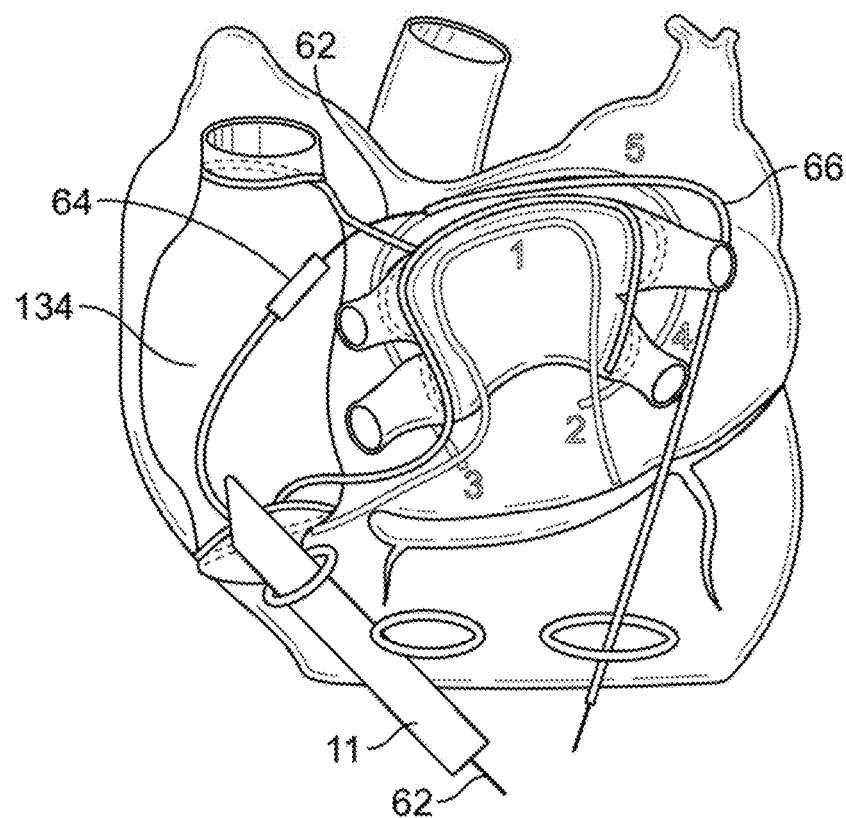
Figure 6O:
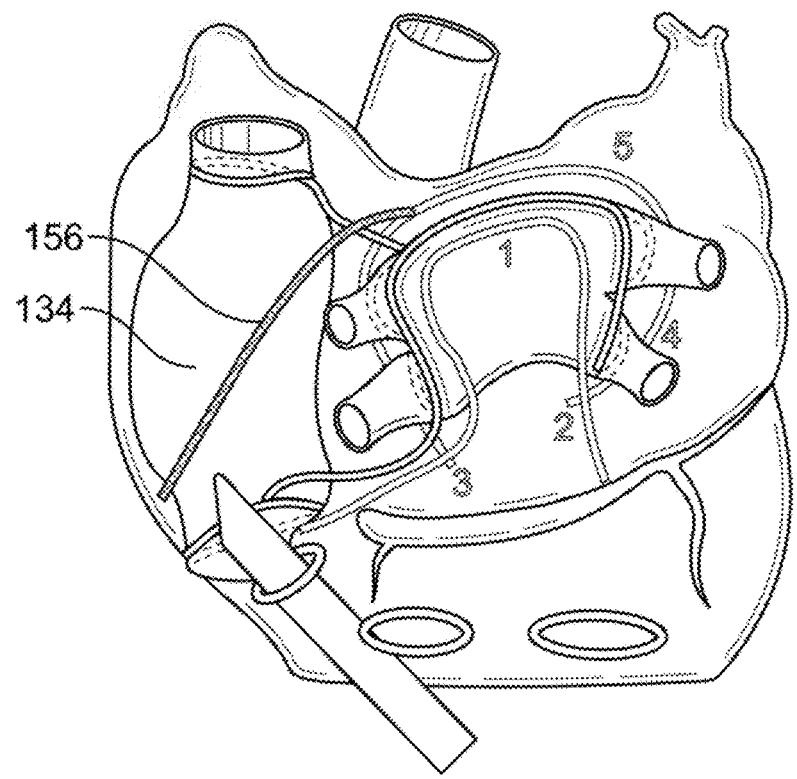
Figure 6P:
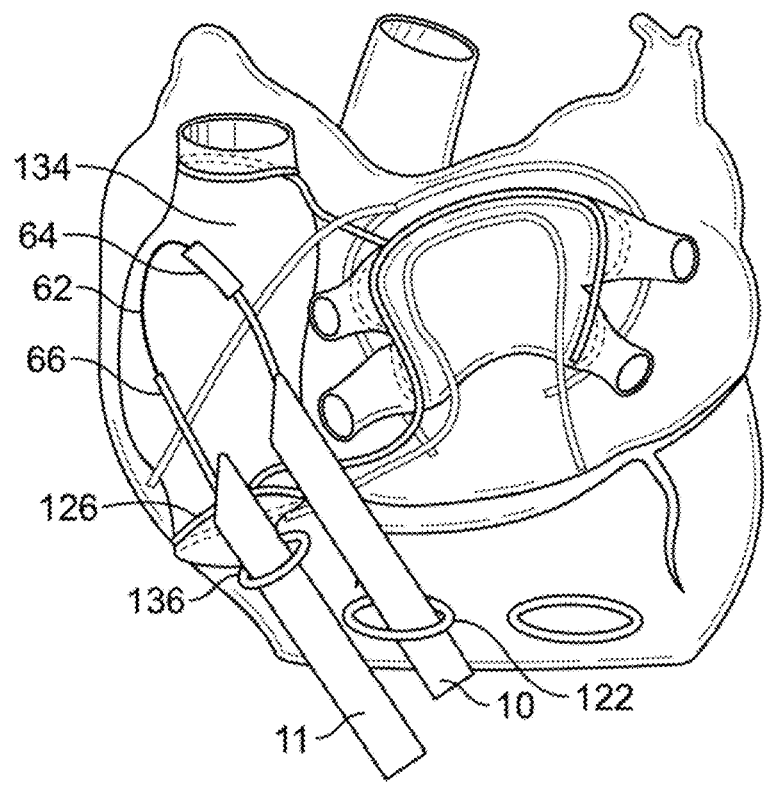
Figure 6Q:
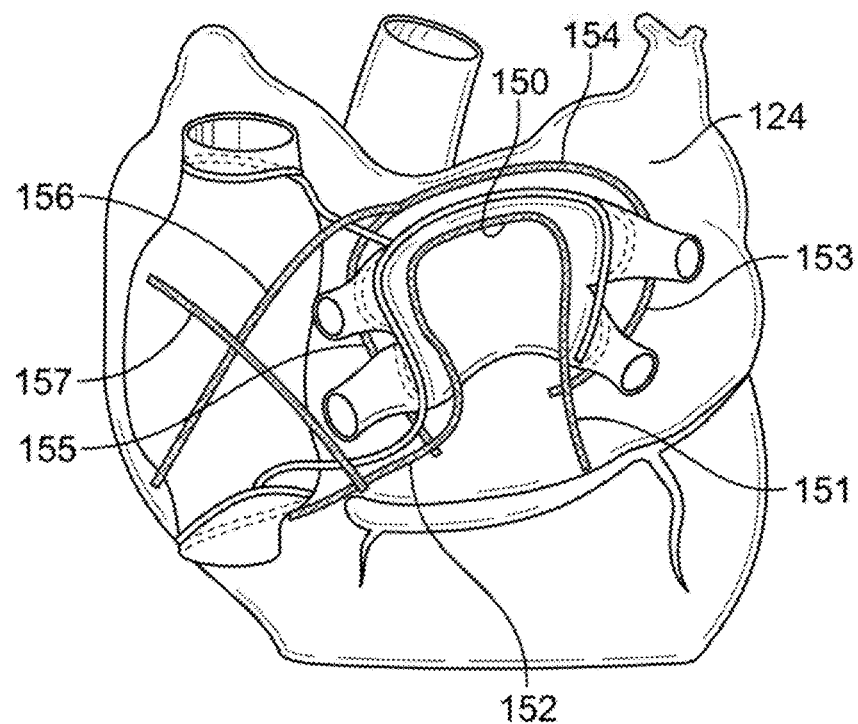

FIGS. 6A to 6Q show one example where the device accesses a posterior surface of the heart 106 and where the multi-mode dissection attributes of the device enable a bi-atrial lesion pattern on a posterior region of the heart. Since the view is from a posterior surface, the notations of right and left are reversed.

As shown in FIG. 6A, the devices 10 are advanced through an epicardium using a left incision 120 and a right incision 122. This allows a distal opening 16 of the devices 10, 11 to be placed into the pericardal space around the left atrium 124.

Next, as shown in FIG. 6B, a catheter 60 (such as a Foley catheter) passes from the right access device 11 to allow a guidewire 62 to be advanced over the left atrium 124. The guidewire 62 is then retrieved into the left cannula 10 using a set of graspers or other similar device. Next, as shown in FIG. 6C, the guidewire 62 passes between the left 11 and right 10 access devices and ultimately extends out of the proximal ends of the access devices 10 11.

Turning now to FIG. 6D, with the guidewire 62 in place, a medical device 64 (such as an ablation device) is advanced over the guidewire 62 and through the right access device 11. The end of the medical device 64 can be optionally viewed with a flexible scope, such as an endoscope or bronchoscope 66 which is also placed over the guidewire 62 from the left access device 10. The medical device 64 can be any energy delivery, ablation, or coagulation device that may be advanced through the access device. Examples of coagulation devices that adhere to irregular contoured surfaces are disclosed below.

The access device 64 can be advanced over the wire 62, to form coagulation lines 150 and 151 on the left atrium (as shown by FIG. 6E). Coagulation line 152 can be created by manipulating the right access device 11 and pulling the device back towards the right access device 11.

FIG. 6F shows repositioning of the right access device 11 with a rigid scope 68 placed therethrough. The combination as well as the features of the device described herein permit dissection through the first pericardial reflection 126 in front of Watterson's groove 128. The scope allows the surgeon to visually navigate through the space as the access device 11 dissects the pericardial reflection 126. This may be accomplished by rotation of the access device 1, which allows a dissection surface to gently dissect the pericardial reflection 126. As shown in FIG. 6G, once through the first pericardial reflection 126, the cannula can advance into Watterson's groove 128 and used to dissect additional tissue to create space for the medical device (coagulation or ablation device). The physician can then advance the access device 11 to further dissect a second pericardial reflection 130 leading into the transverse sinus 132.

FIG. 6H shows a catheter 60 advanced into transverse sinus 132. Once positioned, a larger sized access device 13 or regular cannula can be placed through the left incision 120 for securing a guidewire 62 placed in the Foley catheter (as shown in FIG. 6I). The larger cannula allows both a rigid scope as well as a grasping instrument to be placed within the cannula 13 for viewing and securing the guidewire 62.

FIG. 6J shows the site once the guidewire 62 extends around the pulmonary veins 108 and extends out of the body. The physician can then advance a treatment device 64 over the guidewire 62 from the right incision 122 and a flexible scope 66 advances over the guidewire 62 from the left incision 122. This permits the physician to view the end of the treatment device 64. The physician can then advance treatment device 64 and scope 66 around the guidewire 62 to create coagulation lesions 153, 154, and 155 (in that order, where lesions 153 and 155 cross lesions 151 and 152. This set of lesions, along with lesions 150, 151, and 152 isolates the pulmonary veins from the remainder of the atrium 124 (as shown in FIG. 6K).

Turning now to FIG. 6L, to create lesions on the right atrium 134, the flexible scope 66 can remain within the transverse sinus 132 and the guidewire 62 can be pulled back into the flexible scope—leaving the tip of the guidewire 62 visible to the scope 66. The physician can then advance the scope 66 and guidewire 62 through the pericardial reflection 130 that was previously dissected and over to the right atrium 134.

Next, as shown in FIG. 6M, an access device 11 can be inserted to view and accept the end of the guidewire over the right atrium 134. The access device 11 can be placed either through the previously made right incision 122 or through another higher incision 136 in the pericardium that is over the right atrium 134. The physician then advances the guidewire 62 until an end advances out of a proximal end of the access device 11.

Once the guidewire 62 is accessible from the proximal end of the access device 11, the treatment device 64 can be positioned using the guidewire 62 to create the first coagulation lesion 156 on the right atrium 134 (as shown in FIGS. 6N and 6O)

Next, the physician removes the guidewire 62 from the patient and two access devices 10 and 11 are inserted into either incision in the pericardium 122 or 136. The physician situates the tips of the access devices 10 and 11 over the right atrium 134 as shown in FIG. 6P. The physician may need to further dissect the pericardial reflection 126 on the right atrium with access device 10. Once the physician positions the access devices 10 and 11, the physician passes a guidewire 62 between access devices. A Foley catheter, grasper or any such device (not shown) can be used to assist in passing the guidewire. Once the guidewire 62 forms a loop over the right atrium 134, the physician places the treatment device 64 and the scope 66 through a separate access device 10 and 11. The treatment device 64 and scope 66 can be placed through either access device 10 and 11 depending on the desired location of the coagulation lesion. The physician can then create the final coagulation lesion 157 as shown in FIG. 6R. The final coagulation lesions 156 and 157 each cross the previously made lesions on the left atrium 124 creating the pattern as shown.

FIGS. 7A-7G illustrates another variation of a process to create a lesion (e.g., a bi-atrial lesion) pattern on a heart 106. As show in FIG. 7A, this procedure uses minimal incisions 10 and 11 to access the chest cavity. Such a procedure avoids the need for invasive surgery to open an access the chest cavity or deflating the lungs.

The surgical incisions can be relatively small (e.g., 10 mm or less) to provide access creating atrial lesion patterns. The incisions can be paramedian subzyphoid incisions 10, 11. Additional variations of the procedure contemplate one or more incisions.

Figure 7A:
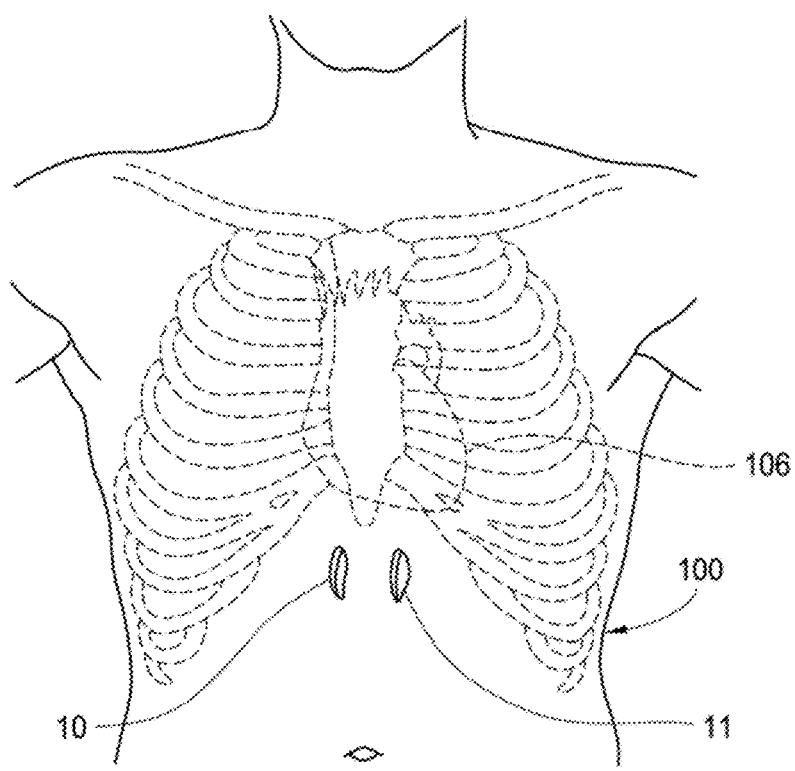
FIGS. 7A-7G illustrates a variation of a procedure to create a lesion pattern via steering of a guidewire and/or an ablation device.
Figure 7B:
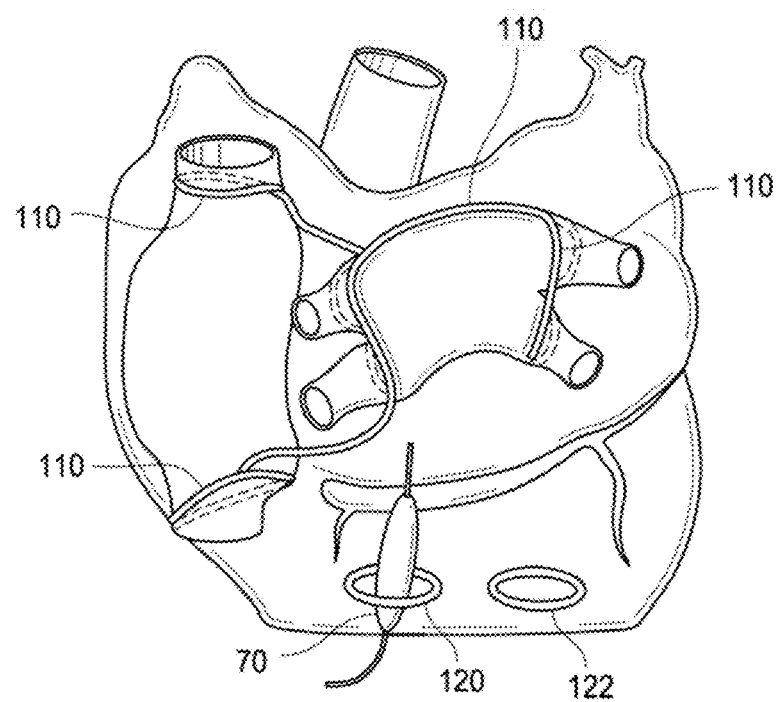
Figure 7C:
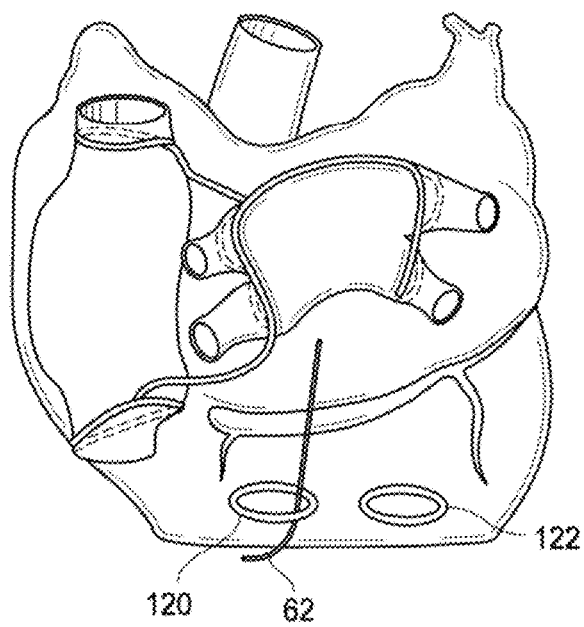

As shown in FIG. 7B, the physician makes two incisions 120 and 122 through the pericardium (not shown) and advances a balloon catheter 70 through one of the incisions. In variations with a single subzyphoid incision a single incision will be made through the pericardium. The balloon catheter 70 can include any commercially available balloon catheter (e.g., an angioplasty catheter) or it can include a catheter specifically designed for this procedure. In most cases, the balloon catheter will have a predetermined shape or will be non-distensible. However, alternate variations are within the scope of this disclosure.

Next, the physician inflates the balloon on the catheter 70 to create space or a path (via repositioning and multiple inflating and deflating of the balloon) to accommodate for insertion of a coagulation device and/or a flexible endoscope. FIG. 7I also illustrates pericardial reflections 110 on the surface of the heart.

The physician then advances a guidewire 62 through one incision 120 and navigates it to the desired treatment area. In one variation of the procedure, the guidewire 62 can be steerable to allow for manipulation and improved positioning.

Figure 7D:
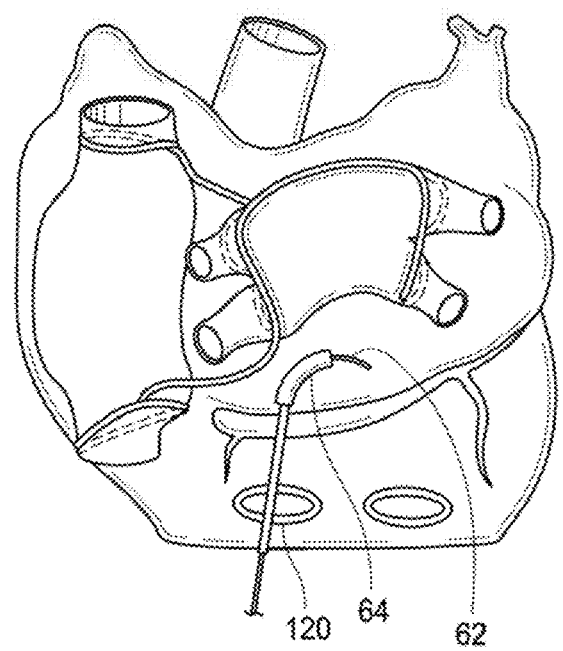
Figure 7E:
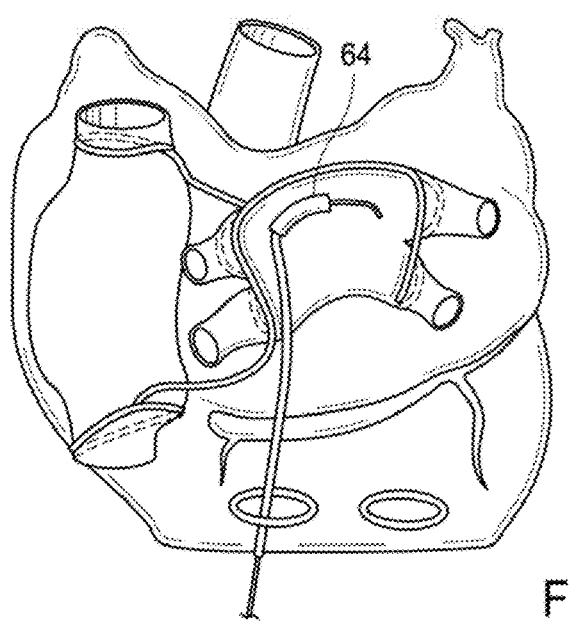

FIG. 7D shows a coagulation device 64 advanced over the guidewire 62. As noted above, the physician can manipulate the guidewire 62 via steering or other means to position the coagulation device 64 at the desired treatment location. Alternately, the physician can steer the coagulation device 64 itself in those variations where the coagulation device 64 incorporates or is coupled to a steering mechanism. A steerable coagulation device 64 permits a physician to use a standard guidewire to position the coagulation device 64 in the approximate treatment area, then the coagulation device 64 can be manipulated or steered to the desired location. FIG. 7E illustrates positioning of the coagulation device 64 at a desired target location.

Figure 7F:
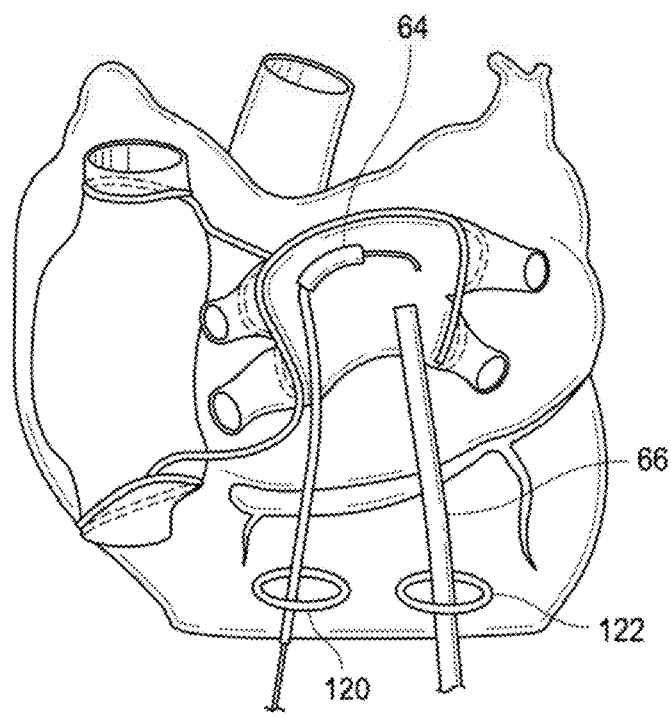
Figure 7G:
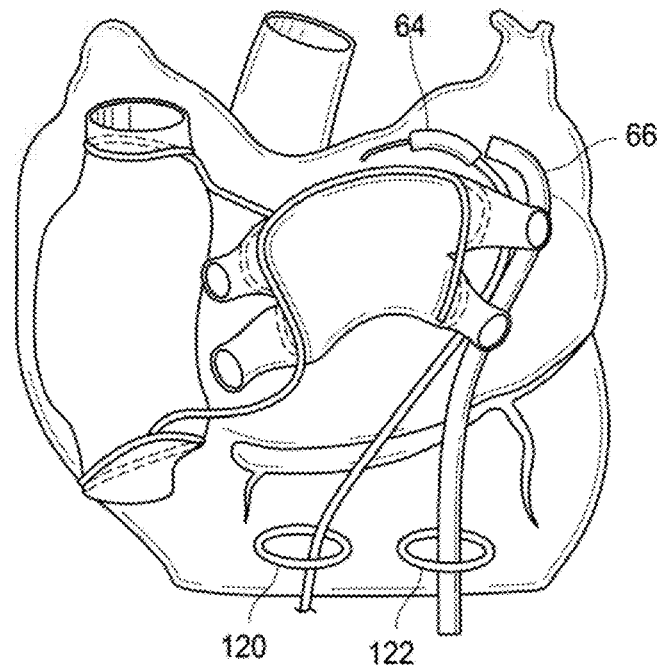

FIGS. 7F and 7G illustrate use of the second incision 122 to advance a second device 66 to assist in the procedure. In some variations, the second device 66 comprises a flexible endoscope that enables the physician to have direct visualization of the working area or of the coagulation 64 device. As shown by FIG. 7G, steering of the guidewire 62 and/or coagulation device 64 allows for positioning of the device 64 and scope 66 to any desired location.

Figure 8A:
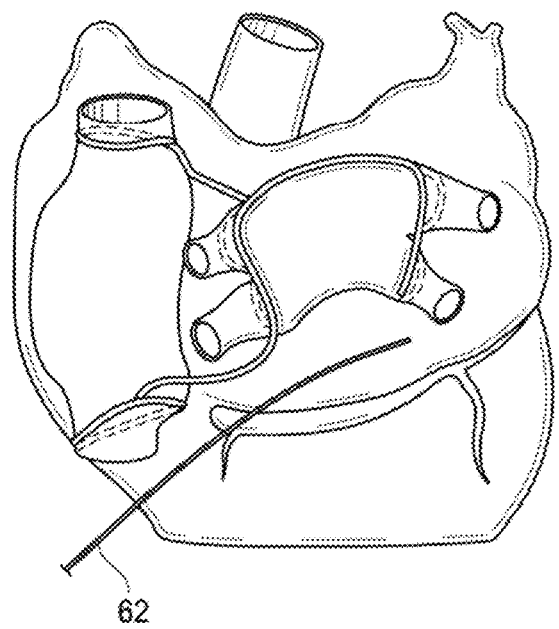
FIGS. 8A-8C illustrate using a guide wire having steering capabilities.
Figure 8B:
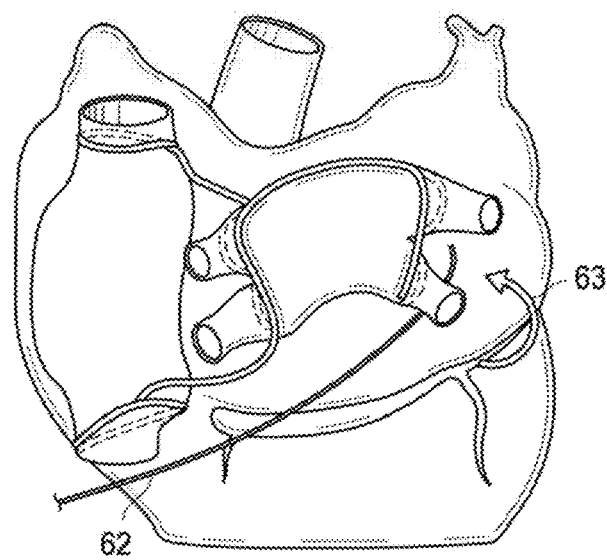
Figure 8C:
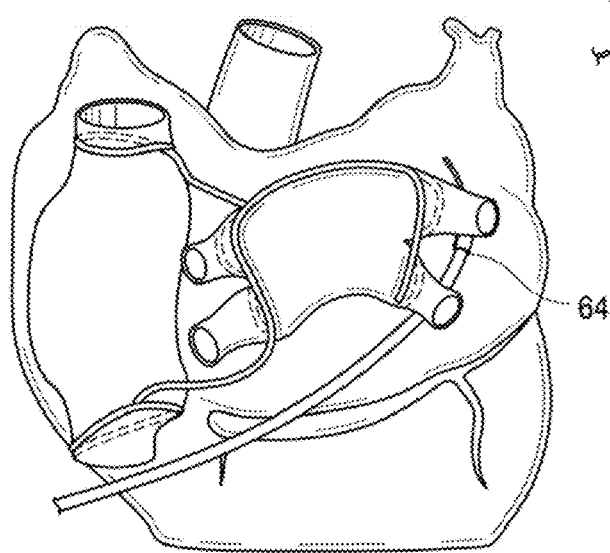

FIGS. 8A to 8C illustrate using a guide wire 62 having steering capabilities. As shown in FIG. 8B, the guidewire can be directed around structures in the body and articulated 63 so that a coagulation device 64 can be advanced over the guidewire to position the coagulation device 64 at the desired location. Variations of the steerable guidewire can have radio-opaque markers to allow of visualization of location while using fluoroscopy or can employ other positioning/location means. The Coagulation device can also have radio-opaque markers to allow visualization under fluoroscopy. Additionally, the coagulation device 64 can have tracking elements built into the distal end to allow for 3 dimensional tracking of the device location. An example of a type of tracking system is described in U.S. Pat. No. 7,096,148 the entirety of which is incorporated by reference herein.

Figure 8D:
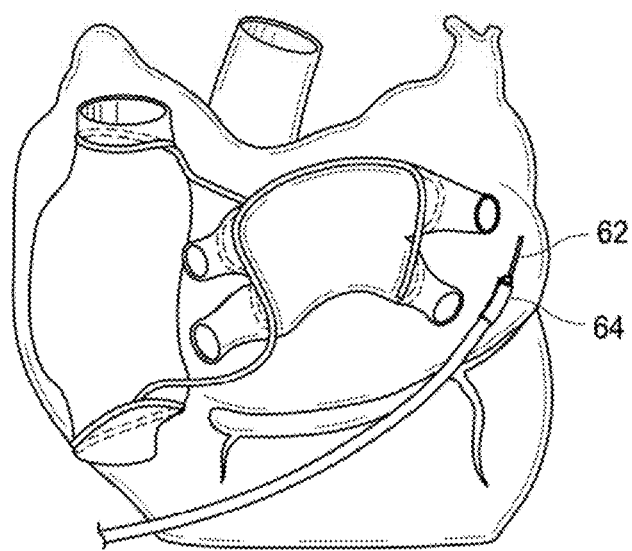
FIGS. 8D-8E illustrate another variation of a procedure where a coagulation device is capable or is coupled to a steering mechanism
Figure 8E:
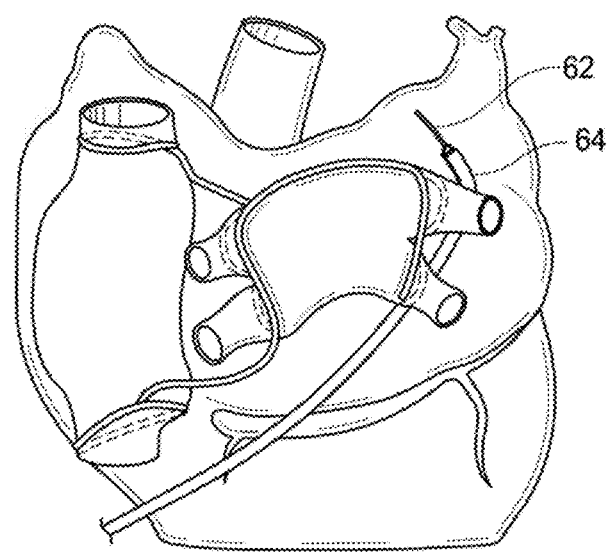

FIGS. 8D and 8E illustrate another variation of a procedure where a coagulation device 64 is capable or is coupled to a steering mechanism. As shown, the coagulation device can be positioned around structures in the body to reach a desired treatment location.

Figure 9A:
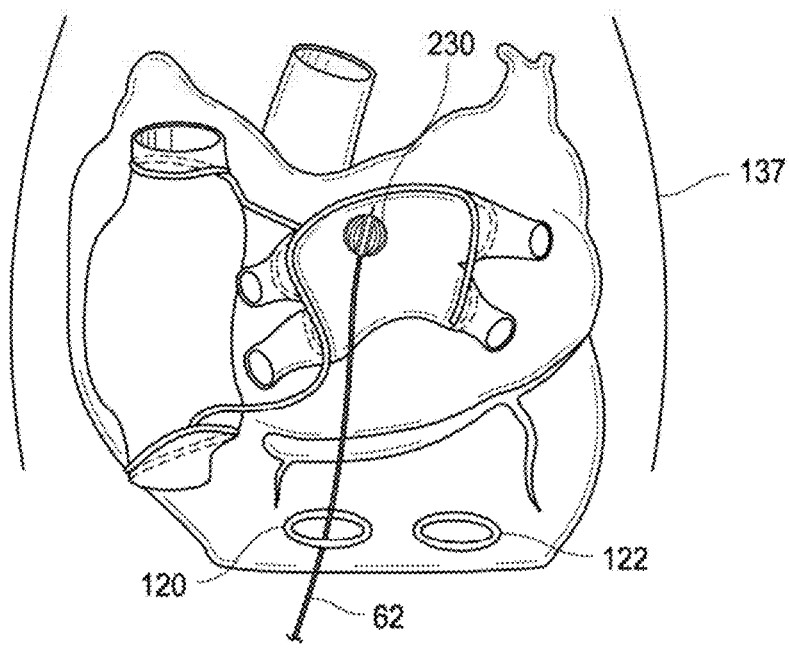
FIGS. 9A to 9E illustrate another variation of a procedure according to the present disclosure in which an expandable member is used to augment or assist in the creation of coagulation lesions.
Figure 9B:
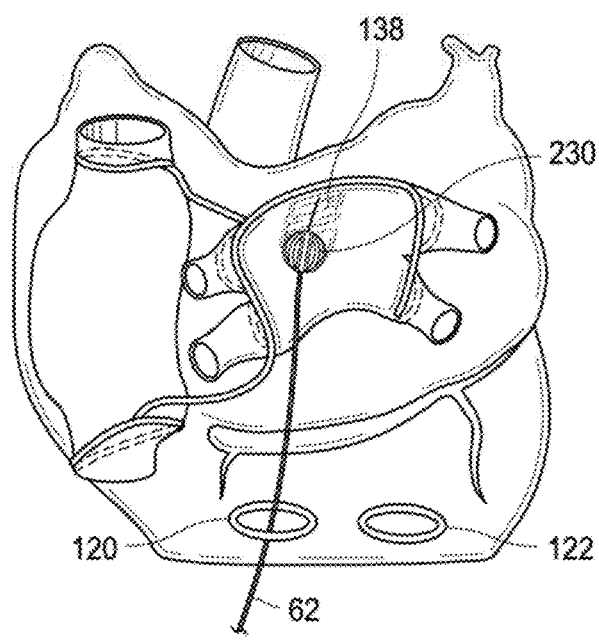
Figure 9C:
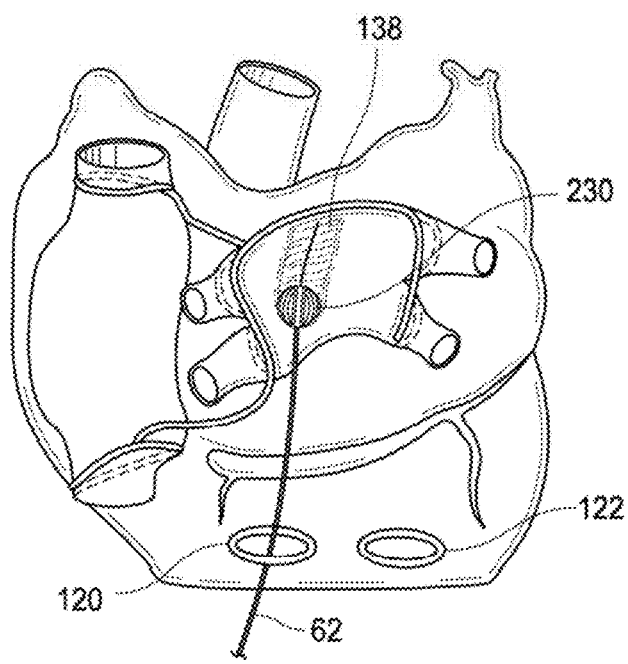
Figure 9D:
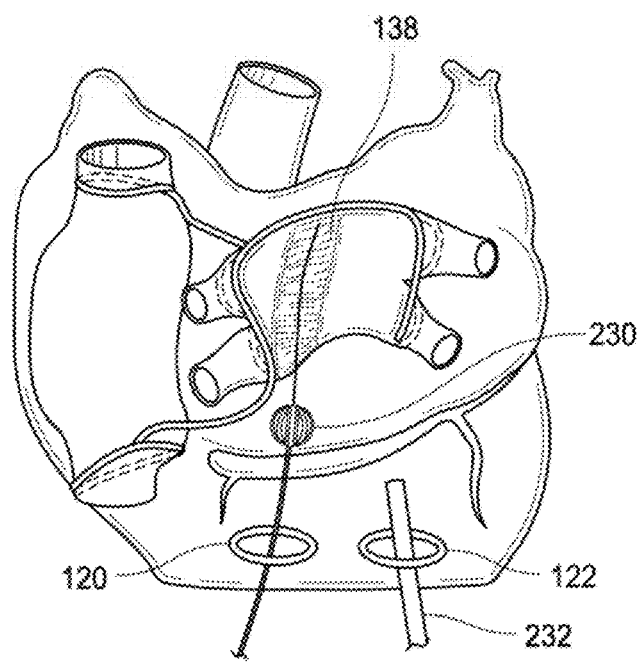

FIGS. 9A to 9E illustrate another variation of a procedure according to the present disclosure in which an expandable member is used to augment or assist in the creation of coagulation lesions. Those skilled in the art readily understand that the heart is enclosed in aconical sac of serous membrane, called the pericardium 137, which encloses the heart and the roots of the great blood vessels. For sake of clarity, the pericardium is not shown as covering the heart in the illustrated figures. The pericardium 137 consists of an outer fibrous coat that loosely surrounds the heart and is prolonged on the outer surface of the great vessels except the inferior vena cava and a double inner serous coat of which one layer is closely adherent to the heart while the other lines the inner surface of the outer coat with the intervening space being filled with pericardial fluid. As shown, one or more pericardium incisions 120, 122 are made in the pericardium 137 to allow advancement of a guide wire 62 over which a physician advances a dilation device. Alternatively, a physician can advance a steerable or otherwise maneuverable dilation device without a separate guidewire or with a guide member directly incorporated therein. The term guidewire is intend to include any wire, catheter, or guide type device whether steerable or non-steerable. Moreover, a coagulation device with a dilation member (as discussed below) can be advanced without a separate dilation device As shown in FIG. 9A, the guide wire 62 or other dilation member advances within the pericardium. The physician expands the dilation member 230, then reduces the dilation member so that it may be repositioned as illustrated in FIG. 9B. Doing so, begins to form a path or channel 138 within the pericardium. The physician then subsequently re-expands the dilation member 230 to extend the channel. This process is repeated as shown in FIGS. 9C and 9D so that the physician forms the desired channel. In alternate variations, the dilation member 230 remains expanded and is withdrawn or advanced to form a channel. Moreover, support devices 232 can be introduced into the pericardium or thoracic cavity to deliver fluid or visualization to the device during channel creation or during actual treatment.

Once the channel is created, as the channel is created (in the event the dilation member is included on the treatment device), the physician can create the desired treatment lesions as described herein.

Figure 9E:
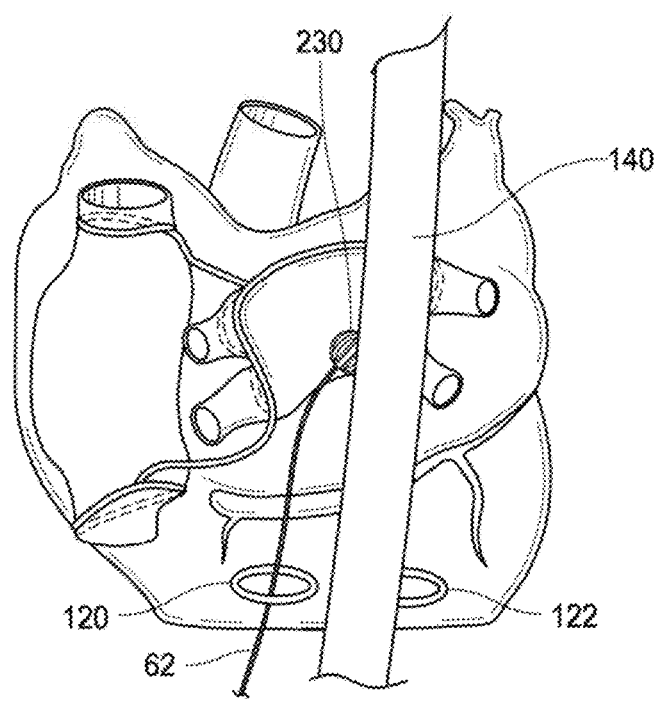

FIG. 9E illustrates another use for a dilation member 230. In this example, the dilation member 230 is used to dissect or separate anatomic structures 140 (e.g., the esophagus, a phrenic nerve, etc.) from the area to be treated in an effort to minimize collateral damage to the structure 140. Alternatively, the expandable member 230 can be expanded or deploy a cooling fluid to preserve the anatomic structures 140. In most cases the structures 140 are exterior to the pericardium. However, expansion of the dilation member 230 within the pericardium is sufficient to dissect or protect the structures.

Any of the devices described herein can be non-invasively imaged or tracked. For example, U.S. Pat. No. 7,096,148 to Anderson et al., the entirety of which is incorporated by references, discloses a magnetic tracking system that can be employed for tracking during the procedure.

Exemplary Treatment Devices

Figure 10A:
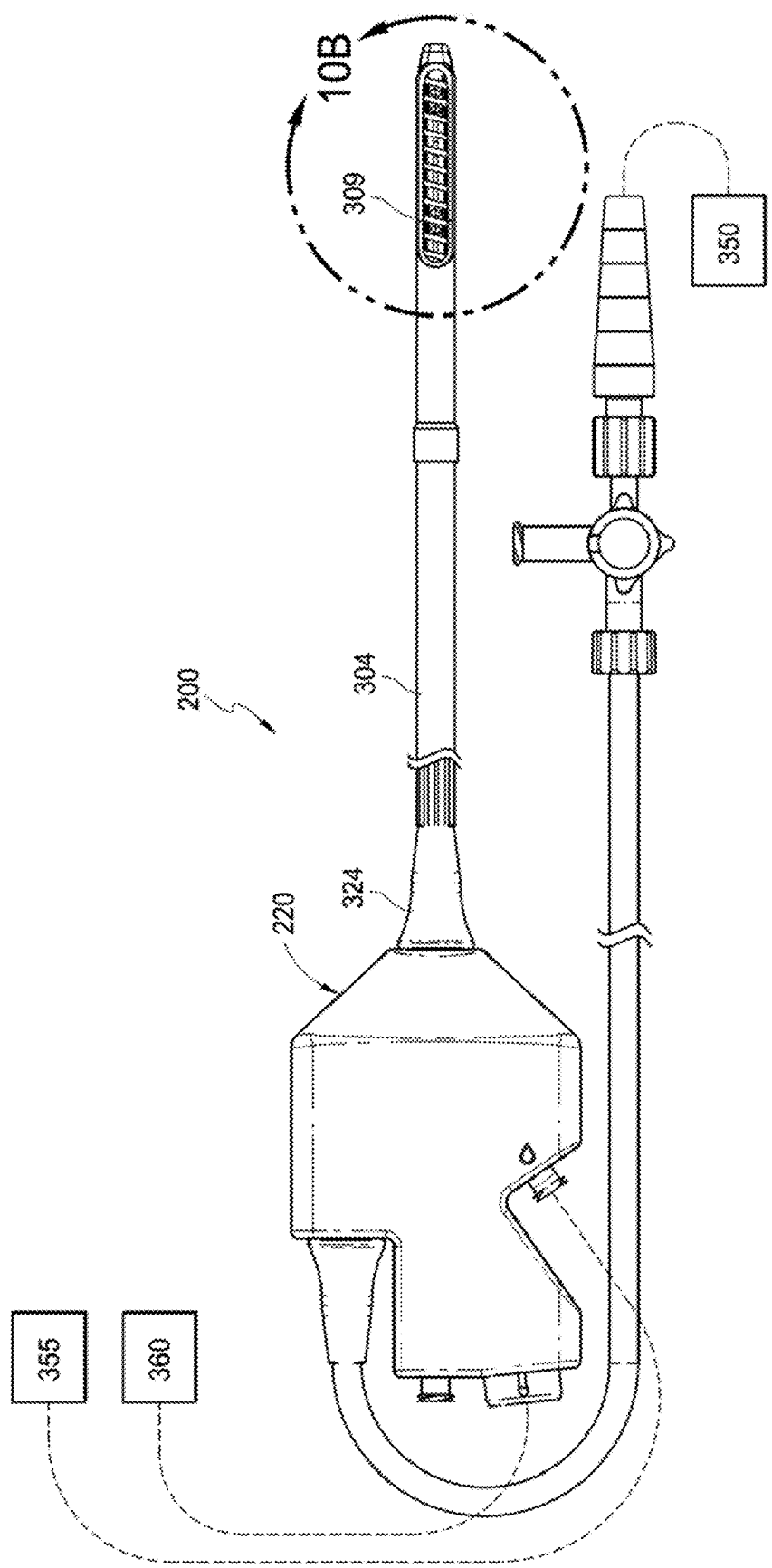

FIG. 10A illustrates another variation of a coagulation device consisting of a probe 200 and a handle 220. In this variation, the probe 200 again includes a shaft 304 having a housing 309 at a distal section of the shaft 304. However, the variation of FIG. 10A shows a variation of a coagulation probe 200 having the capability of pacing and/or sensing as well as an element coupled to a single probe. As described above, variations of the coagulation device can employ any variety of shapes and sizes for the handles and/or housing. In the example shown, the handle 220 includes a plurality of connectors for connecting the probe to a power supply 360, a fluid source 355 and a vacuum source 350. The device can also include a strain relief 324 as well as any other features to accommodate flexibility of the shaft.

Figure 10B:
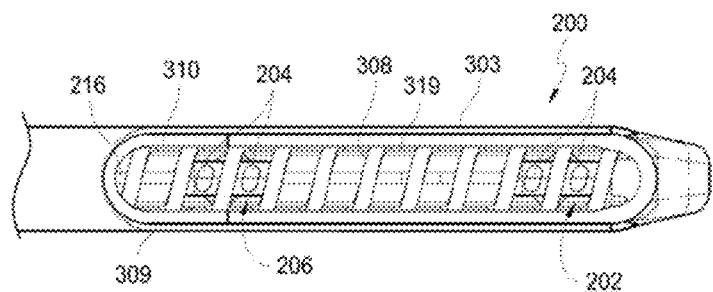

FIG. 10B illustrates a magnified view of the distal end of the probe 200 of FIG. 10A. In this variation, the probe 200 includes a housing 303 having both an energy transfer element 308 and a plurality of diagnostic element assemblies 202 and 206 exposed at the opening 310 of the housing 303. The illustrated variation shows a probe 200 having a coiled energy transfer element 308 with two diagnostic element assemblies 202 and 206. However, additional variations of probes can include a non-helical energy transfer element 308 with any number of diagnostic element assemblies or even a single assembly. As shown, electrodes 204 on the diagnostic element assemblies 202, 206 are positioned between the electrode or element surface (in this case the turns of the coil.) As described herein, the areas between the turns of the coil permit a vacuum force within the housing to secure the opening against tissue and draw the tissue into opening so that tissue contacts the energy transfer element 308 as well as the diagnostic electrodes 204. The housing 303 can also include a flexible lip 309 or extension that assists in securing tissue against the opening 310 to form a vacuum. In some variations of the device it important that the electrodes 204 on the diagnostic assemblies remain electrically isolated from the energy transfer element 308. This can be accomplished by positioning the diagnostic electrodes 204 within the spacing of the element 308 as well as electrically insulating the interior of the element 308. As shown below, the probe 303 can include one or more liners 319 that can support the helical element 308 and/or provide additional insulation to electrically isolate the diagnostic electrodes 204.

Figure 10C:
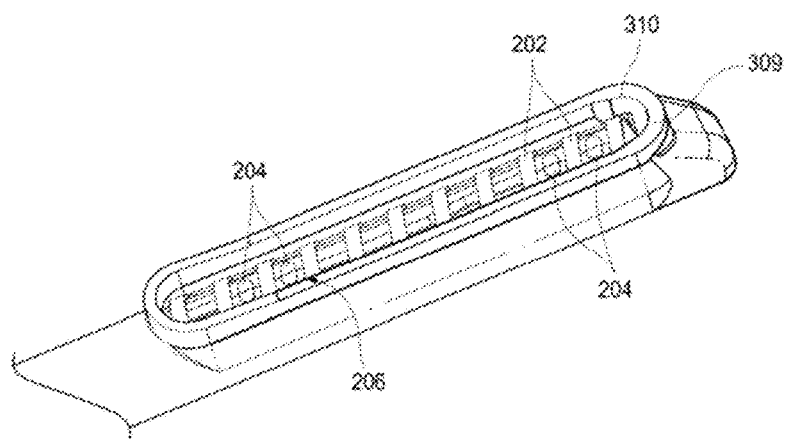

FIG. 10C shows a perspective view of the energy transfer element 308 located within an opening 310 of the probe 200. As shown, the energy transfer element 308 and diagnostic element assemblies 202 and 206 are recessed within the opening 310 so that when the lip 309 forms a seal against tissue the tissue is drawn into the opening 310 and engages the element 308 and electrodes 204 of the diagnostic assemblies 202 and 206.

FIG. 10D illustrates a perspective view of a steerable catheter 234 with a rapid exchange tip 236 that accommodates a guide wire 62. The guide wire can advance through the treatment device 200 allowing the physician to use conventional techniques to advance the device 200 through the channel or into the epicardial sac. FIG. 10E illustrate a bottom view of the steerable catheter 234 and treatment device 200 of FIG. 10D.

Figure 10F:
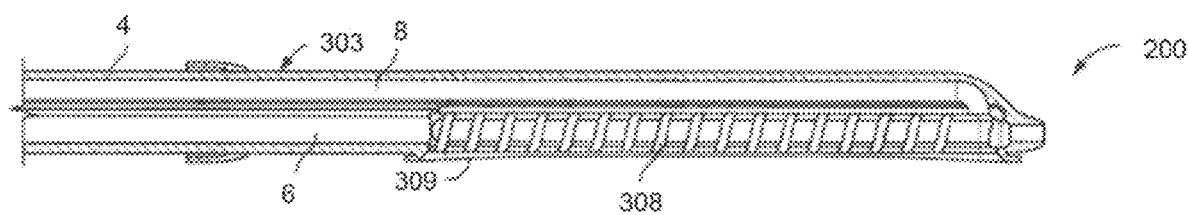

FIG. 10F illustrates a side-cross sectional view of a probe 200. As illustrated, an elongate shaft 4 contains an elongate housing 303. The housing 303 includes an element 308 within the housing 303, where the element 308 is exposed at the bottom of the housing 303 via an opening. In this variation, the element 8 is located within the main lumen 6 which is in fluid communication with the vacuum source 350 of FIG. 10A such that it functions as a vacuum lumen. Fluid flows from a fluid source 355 and is drawn through the fluid perfusion lumen 8 across the opening and back into the vacuum lumen 6. If seal is not formed against the soft tissue, then fluid does not flow. Accordingly, the confirmation of fluid flow (or the audible noise confirming a closed fluid circuit) allows the medical practitioner to confirm adequate tissue engagement between the device and tissue. Once adequate engagement is confirmed, the practitioner can energize the electrode during the fluid flow to create the lesion. Breaking of the seal between the opening and the tissue will stop the fluid flow. Accordingly, the presence of fluid flow can serve as confirmation of sufficient engagement with tissue.

The integrated vacuum coagulation probes provided by nContact Surgical, Inc., North Carolina are examples of devices that allow intimate contact specifically between a soft tissue surface and the energy portion of the device. In those examples, the electrode(s) used to transmit energy (radiofrequency or ultrasonic) is capable of heating the soft tissue until achieving irreversible injury making the soft tissue non-viable and unable to propagate electrical impulses, mutate, or reproduce. These integrated vacuum coagulation probe embodiments may be in conjunction with the access devices described herein to treat atrial fibrillation, ventricular tachycardia or other arrhythmia substrate, or eliminating cancer in lung, or other soft thoracic tissue by destroying target cells.

Figure 11A:
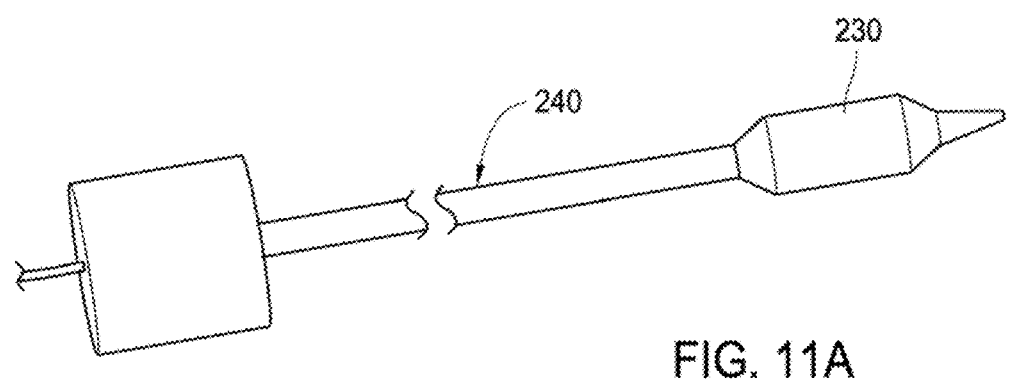
FIGS. 11A to 11C show variations of dilation devices.
Figure 11B:
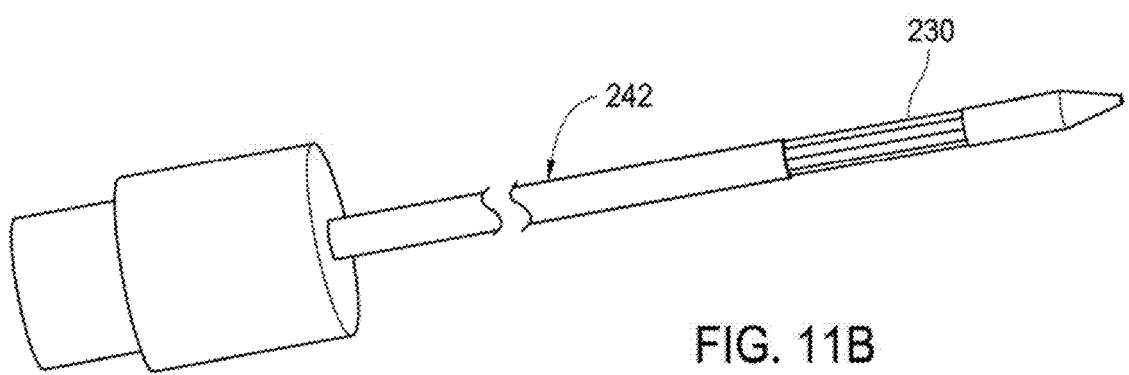
Figure 11C:
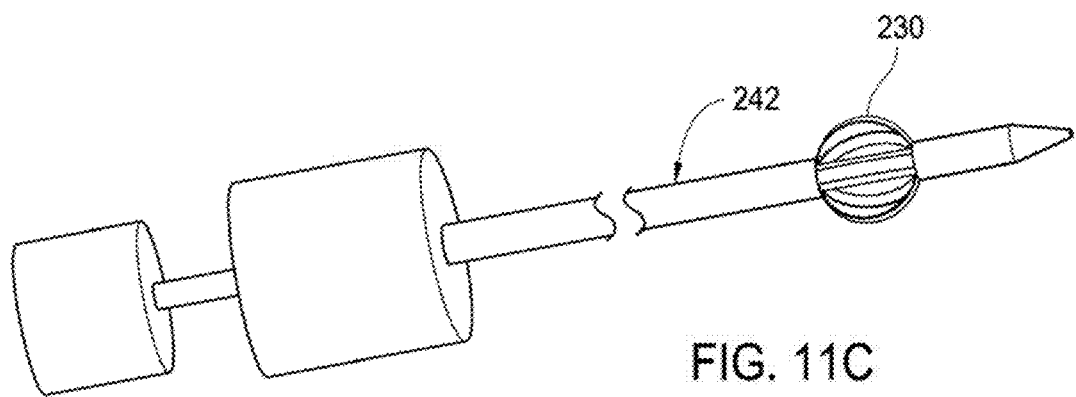

Examples of such probes are disclosed in commonly assigned U.S. applications, publications and patent cited above Exemplary Dilation Devices FIGS. 11A to 11C provide basic examples of dilation devices having dilation members 230 for use as described herein. FIG. 11A illustrates a sample balloon catheter 240 with an expandable member 230 shown in an inflated state. The balloon can be configured to deliver fluids through the expandable member 230. Variations of the balloon catheter 240 include distensible and non-distensible balloons. FIG. 11B illustrates a mechanically expandable basket device 242 having a dilation member 230 that comprises an expandable basket as shown in FIG. 11C. The basket device 242 can also be configured to deliver fluids through the dilation member 230 or through another port. Typically, the shafts of the devices is flexible to allow for navigation to the desired target site. Furthermore, any of the devices can accommodate a flush lumen to deliver or remove fluid from or near the target area.

FIG. 12A illustrates another variation of a treatment device 200 as described herein that can advance over a guidewire 62. FIG. 12B illustrates a front view of the device 200 of FIG. 12A. As illustrated, the guidewire can enter and an exit at a working end of the treatment device 200. Furthermore, variations of the device include a guide wire 62 having dilation members 230 placed thereon and as shown in FIG. 12C. This feature permits direct channel creation using the guidewire alone or as the treatment device 200 advances through the epicardium.

Figure 12F:
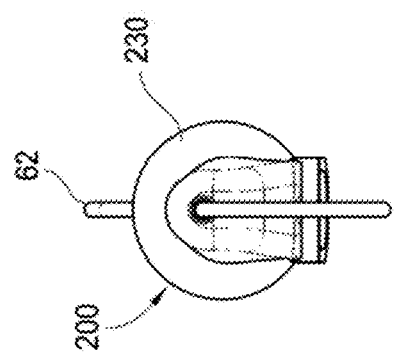
FIG. 12D to 12F illustrate an example of a treatment device having a dilation member located on a working end of the treatment device.
Figure 12D:
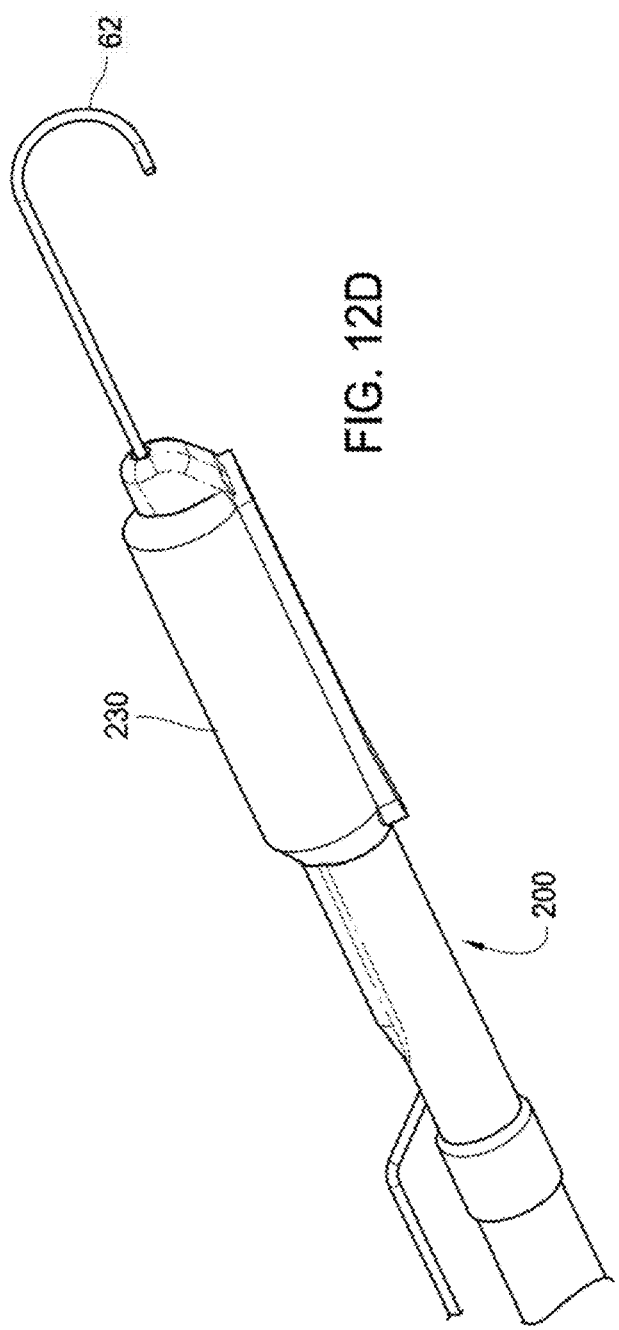
Figure 12E:
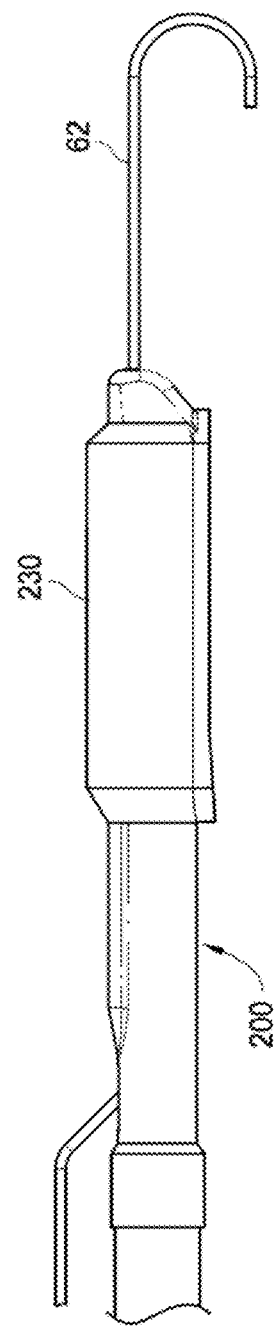

FIG. 12D illustrates another variation of a treatment device 200 that includes an expandable member 230 that is incorporated at the working end of the treatment device 200. As shown, the guidewire advances through the working portion as well to allow use of the guidewire and treatment device for creating the path or channel though the pericardium as described above. FIGS. 12E and 12F show side and front views respectively of the device 200 and dilation member 230 of FIG. 12D.

Traversing the Epicardial Space

The ability to traverse the pericardial space under direct visualization and create linear lesions throughout the right and left atria has been confirmed clinically using the Numeris® Guided Coagulation Device manufactured by nContact Surgical. The vacuum-integrated device ensures energy is directed only against tissue engaged by the opening in the device that exposes the electrode. This orientation is confirmed under endoscopic guidance during the convergent procedure.

In those cases where there is a need for a pericardial window, a surgeon creates the paracardioscopic access and manipulates the devices using endoscopic visualization. To migrate epicardial ablation to the electrophysiology, the need for a pericardial window and endoscopic visualization can be eliminated.

As such a subxyphoid access as described herein and diagnostic features incorporated on the device allows access through the pericardium using a traditional pericardiocentesis approach, manipulation over a guidewire throughout the pericardial space, and assurance of device and electrode orientation using diagnostic electrodes capable of coupling to 3-D Navigation Systems and EP Recording System.

After percutaneously inserting a needle subxyphoid through the pericardium a guidewire is inserted into the pericardial space. Contrast is injected to confirm position of the guidewire in the pericardial space.

Figure 13A:
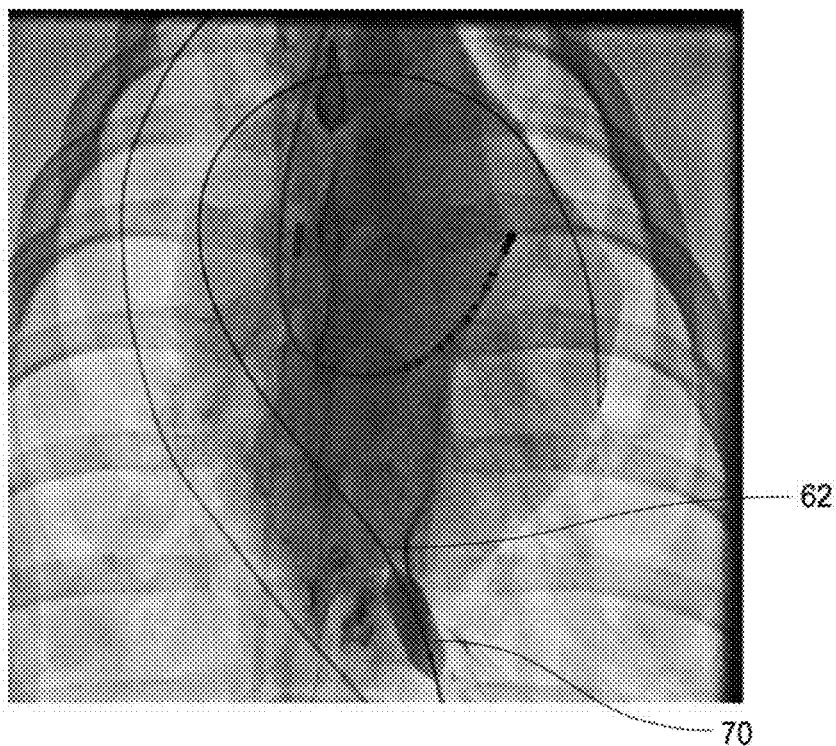
FIG. 13A shows a radiological image of a balloon catheter advanced over a guidewire and into the pericardial access site.

As shown in FIG. 13A, a balloon catheter 70 is advanced over the guidewire and into the pericardial access site. In one example, a 10 mm balloon is inflated to open the puncture through the pericardium to allow the coagulation device to pass without the need for a sheath or trocar. The balloon is repositioned (retracted or advanced) and inflated in sequential movements to create a channel through which the ablation device can be advanced over the guidewire 62.

Figure 13B:
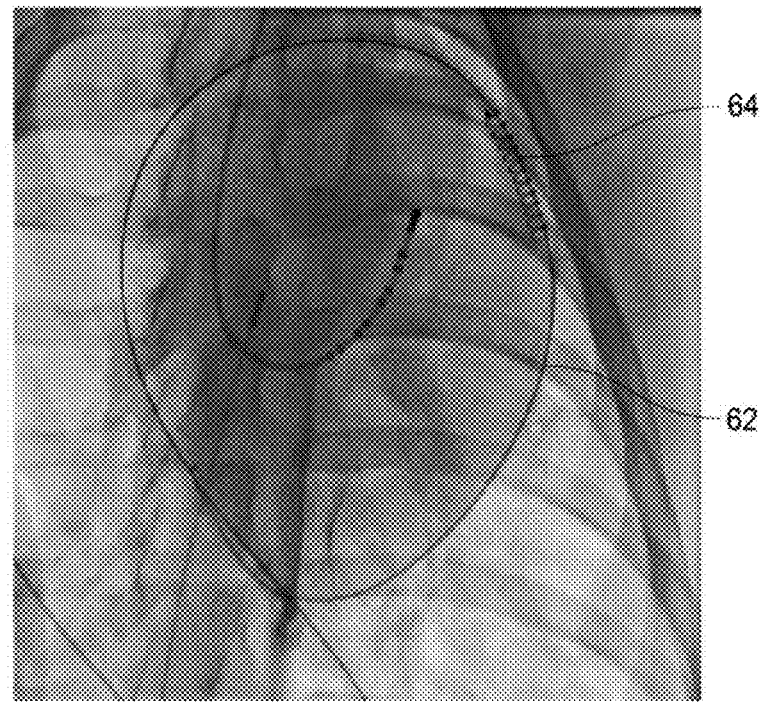
FIG. 13B shows a radiological image of a coagulation device advanced over a guidewire when positioned against a left atrial appendage.

FIG. 13B shows a radiological image of a coagulation device 64 (where only the coil is visible in the image) advanced over a guidewire 62 when positioned against a left atrial appendage. After obtaining access, the coagulation device can be advanced percutaneously over the guidewire and through the pericardial opening. The device can be manipulated along the guidewire into the desired ablation locations (atrial or ventricular). The device has excellent torque response and column strength to traverse throughout the pericardial space over the guidewire that directs the device along the pericardium.

Diagnostic electrodes incorporated along the ablation coil electrode of the device ensure the ablation electrode engages the desired cardiac tissue. The diagnostic electrode bipolar pairs are coupled to a 3-D Navigation system using impedance to provide location information. Electrograms can be obtained to determine tissue (atrial and ventricular) that the ablation electrode contacts and evaluate lesion creation by observing the reduction in electrogram amplitude throughout the ablation process.

The vacuum ensures the device contacts tissue, the electrograms reduce the need for endoscopic guidance and provide information on location and effect of lesion creation. The combination of both enables performing atrial and ventricular ablation through percutaneous, subxyphoid puncture which EPs are comfortable.

The following outline details an example of an access procedure in accordance with a subxyphoid approach:
  1) Insert needle percutaneously through pericardium and into pericardial space 2) Inject contrast through needle to insure the end of the needle is in the pericardial space not in the heart or outside of the pericardial space.
3) Insert guide wire though needle, remove needle
4) Insert dilator over guidewire (any conventional dilator can be used, see below for examples of different types of dilators) to create opening or the catheter or a sheath
   a. Dilators
      i. Dilators with balloons
         1. Additional features of balloons or other expandable mechanism
            a. Enable creating a channel by sequential inflation/deflation of the balloon along the access path.
            b. Separate anatomical structures from the heart
               i. Phrenic nerve
               ii. Esophagus
            c. Cool the balloon during RF or other heating mechanism (or warm when using cryo) to protect collateral anatomy during endocardial ablation
            d. Insert endoscope into balloon to provide visualization
            e. Inject contrast to show location of balloon
            f. Incorporate electrodes axially along balloon catheter to couple to 3-D navigation system to localize position
            g. Dissect anatomic structures such as the transverse sinus to create a channel
      ii. Dilator with splines
   b. Create a channel (without a sheath) to introduce the catheter into the pericardial space
   c. Use sheath to get access to the pericardial space this sheath stays in place
5) Creating multi-pole ports into the pericardium
   a. Same access procedure
   b. Reasons for multiple ports (see multi port folder)
      i. Add a scope to visualize the device
      ii. Add a "drain" to remove pericardial fluid
      iii. Add a circulating flush to create a layer of fluid between the heart and the pericardium
         1. Possible benefits
            a. Separate anatomical structures from the heart
               i. Phrenic nerve
               ii. Esophagus
            b. Cool the ablation catheter for RF or other heating mechanism
            c. Cool the epicardial surface during endocardial ablation involving RF or other heating mechanism (or warm when using cryo)
            d. Add steroids or other pharmaceutical to help with the healing after ablation
            e. Maintain visualization (aka arthroscopic procedures involving continuous irrigation with saline) within pericardial space
            f. Create space to provide visualization within pericardial space
6) Positioning catheter onto the heart
7) Once the channel is created position Guidewire into desired location
   a. Use steerable Guidewire to navigate to location
   b. Use steerable sheaths to navigate Guidewire to location
      i. Maintaining the Guidewire in place
      ii. Remove sheath and introduce catheter
      iii. Advance to desired location
   c. Steerable catheter with a guidewire lumen to position the guidewire
      i. Remove steering catheter and introduce ablation device
   d. Positioning catheter with the guidewire attached to the distal end.
      i. Positioning catheter stays in place and the ablation catheter is advanced over the wire. Fixed Guidewire (GW)
   e. Rapid exchange steerable catheter with GW
   f. Steerable Catheter can also have a distal balloon
8) Catheter can have steering to aid in positioning
9) Ablation catheter can have a "rapid exchange" lumen for the guide wire so a catheter can be placed proximal to the ablation location
10) Diagnostic electrodes aid in positioning
    a. Ensuring we are in contact with the heart not pericardium
    b. Pace to stimulate the phrenic nerve (if this happens do not ablate there)
    c. Signal decrease as the tissue is ablated
11) Radio-opaque marker on the ablation side of the ablation catheter
12) Balloon on the ablation catheter opposite the ablation coils
    a. The balloon can be filled fluid
       i. Radio-opaque
       ii. Circulation saline

EXAMPLES

Figure 14A:
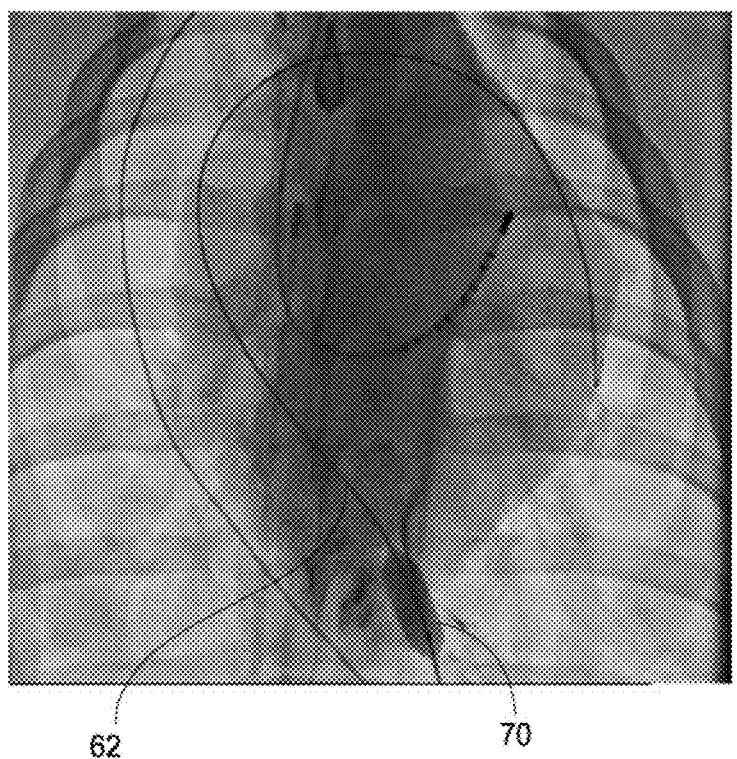
FIGS. 14A to 14F show radiological images of coagulation devices when creating lesions on various atrial surfaces.
Figure 14B:
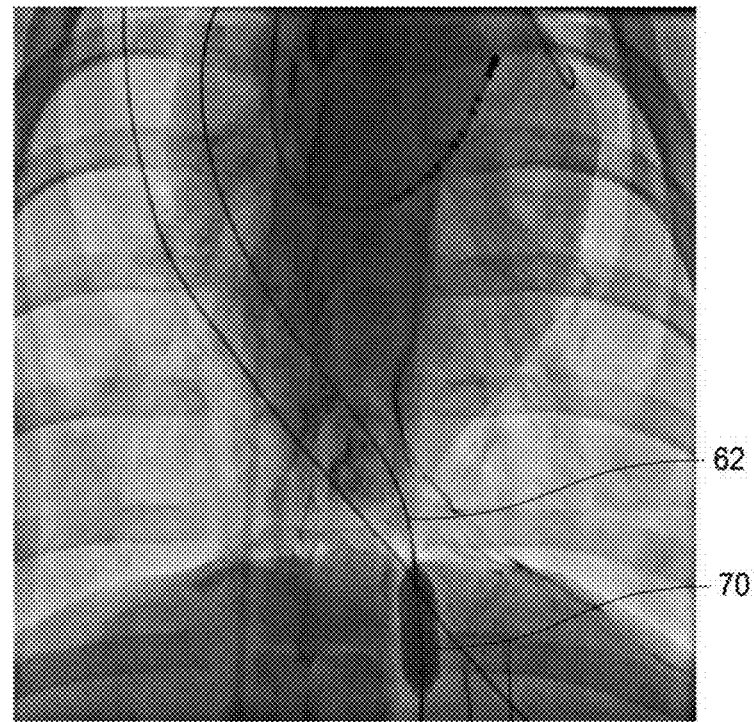

FIGS. 14A to 14F illustrate radiological images of exemplary procedures for subxyphoid introduction of coagulation devices. FIG. 14A illustrates the insertion of a guided device into the pericardium over a guidewire 62. The physician performs a pericardiocentesis and inserts an into the pericardial space. Then the physician advances a guidewire through the needle into the pericardial space. A balloon catheter 70 that is advanced over the guidewire is inflated to open the pericardial access site. The physician then retracts the balloon 70 to create a channel allowing for advancement of a coagulation or other treatment device over the guidewire and into the pericardial space.

Figure 14C:
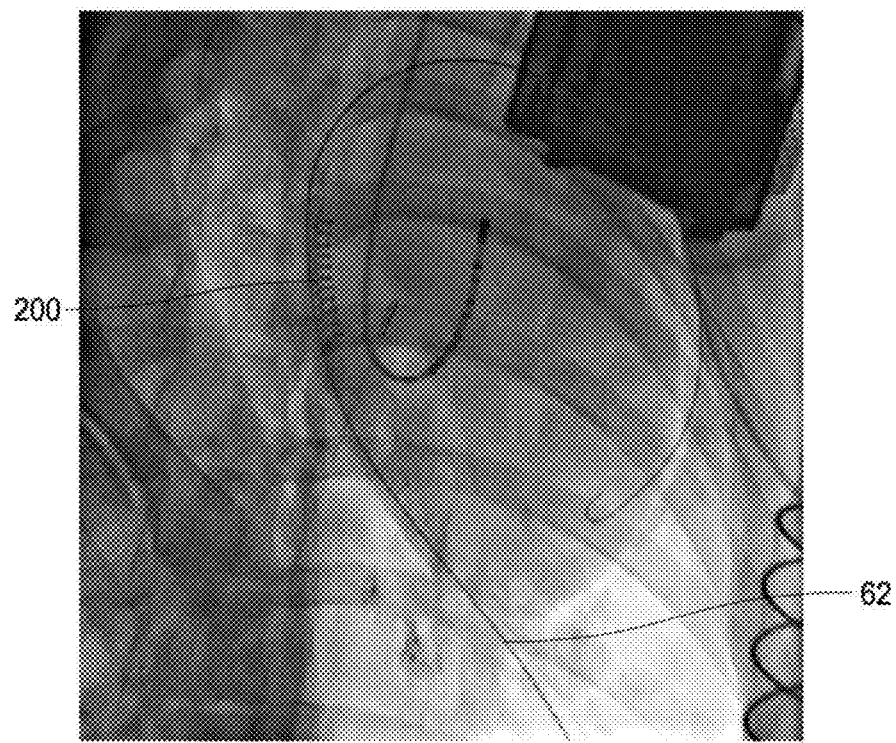

FIG. 14C shows an example of creation of right atrial lesions. The physician manipulates the treatment device 200 within the pericardium against the right atrium. The physician then positioned the device 200 is over the guidewire and along the right atrium. The devices 200 guidewire lumen (located 180° opposite the exposed electrode) is positioned away from the atrium and the vacuum applied from the device 200 pulls the exposed electrode against the atrium. Diagnostic electrodes along the Coil Electrode permit 3-D Navigation and ensure the ablation electrode engages the desired target atrial tissue.

Figure 14D:
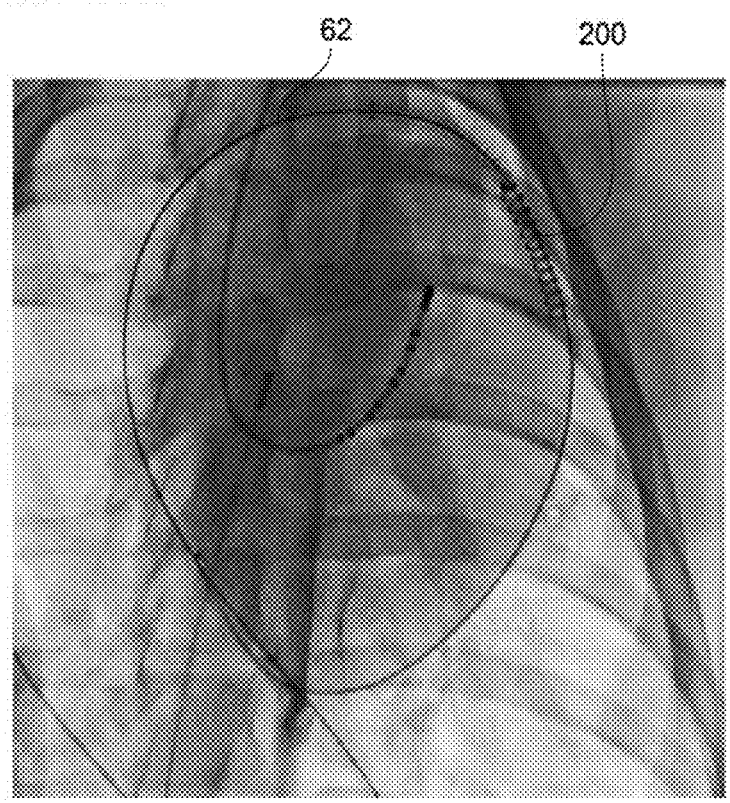

FIG. 14D illustrates creation of the left atrial appendage lesion. The physician manipulates the device 200 within the pericardium and against the left atrial appendage. This may be performed using the guidewire 62. Next, the physician orients the guidewire lumen of the device 200 away from the left atrium so that the ablation or treatment element contacts the left atrium. The physician can use impedance based 3-D navigation to show the location of device 200.

Figure 14E:
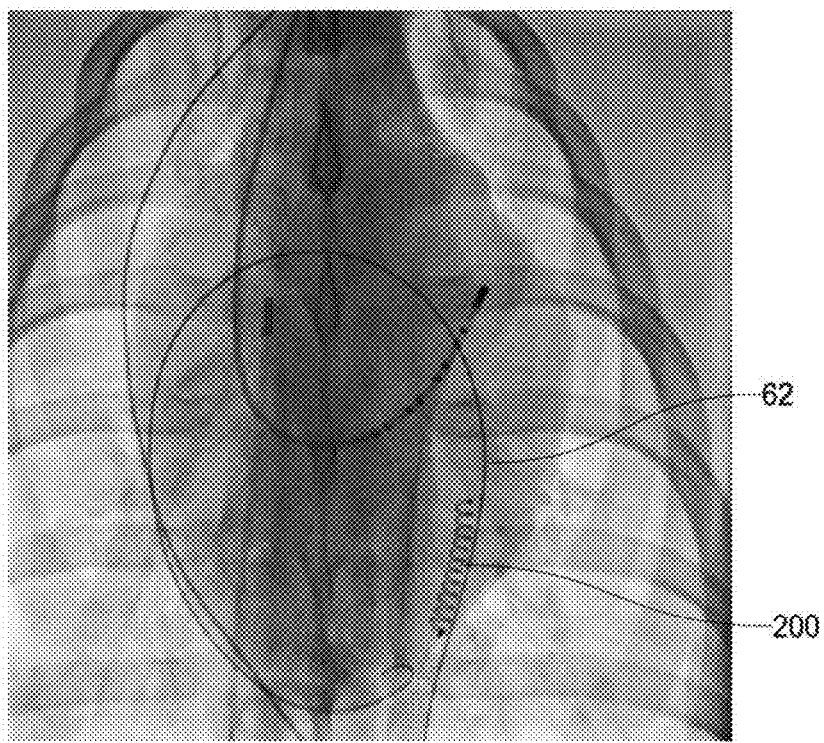
Figure 14F:
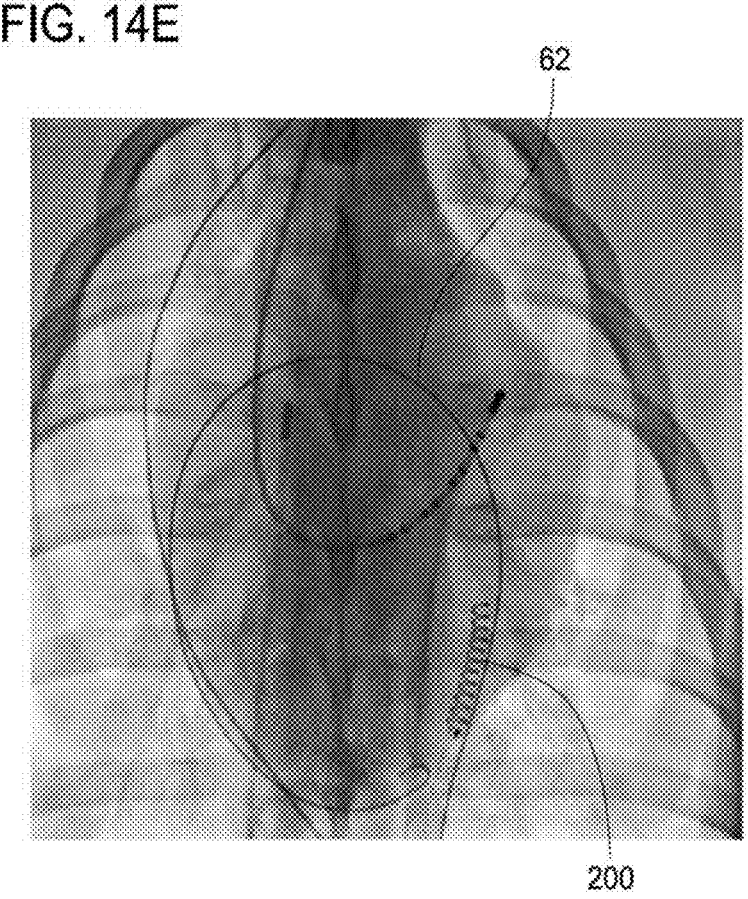

FIG. 14E shows an image from a procedure that created a left ventricular lesion. The physician manipulates the device 200 within the pericardium and against the left ventricle. The physician then orients the guidewire lumen of the device 200 away from the left ventricle so that the ablation electrode is adjacent to the left ventricular surface. The physician can then use impedance based 3-D Navigation to shows the location of the device 200. FIG. 14F shows a device 200 that is used to create a left ventricular lesion in the manner described above and against a base of the left ventricle.

In each of the above cases, electrograms provide location information to ensure that the electrode engages the desired tissue. In addition, after creation of the lesion, the physician can use electrogram amplitude reduction to confirm lesion creation In addition, these integrated vacuum coagulation devices may be used to heat soft tissue along the posterior heart surface resulting in heat-induced contraction of collagen in such tissue thereby resulting shrinking of said soft tissue. For example, heating the mitral valve annulus along the posterior atrio-ventricular groove may induce shrinking of the annulus thereby correcting mitral valve regurgitation. However, it is understood that the invention is not limited to the above described vacuum coagulation probes. Instead, any number of coagulation, ablation, or surgical devices may be used as required.

Multi-Lumen Perfusion Device

Figure 15A:
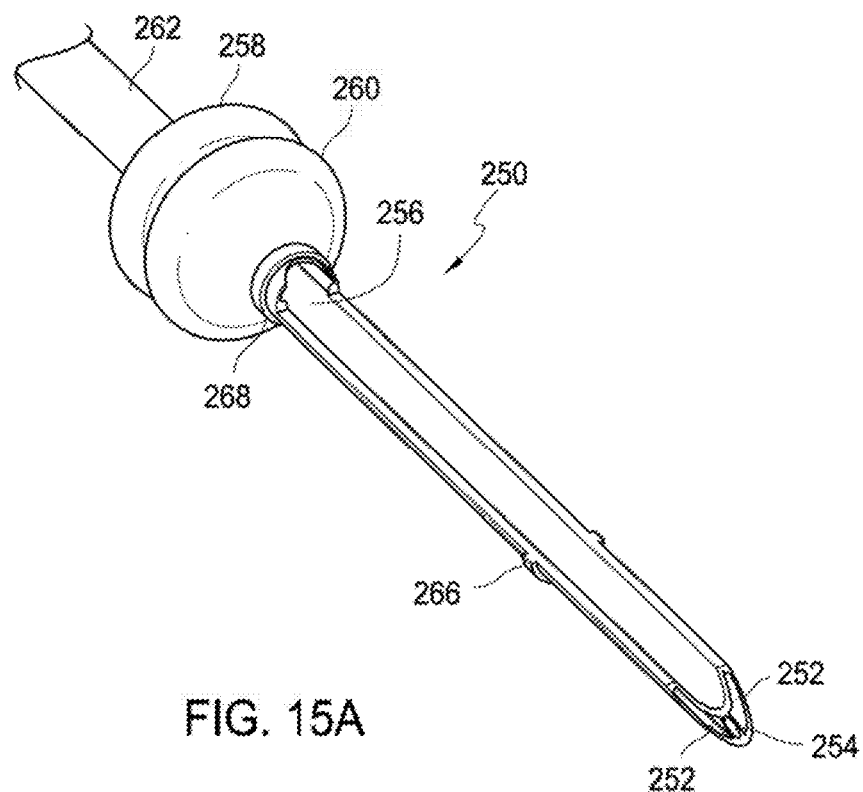
FIG. 15A to FIG. 15C illustrate a perfusion device useful in the procedures described above requiring perfusion of the pericardial space.
Figure 15B:
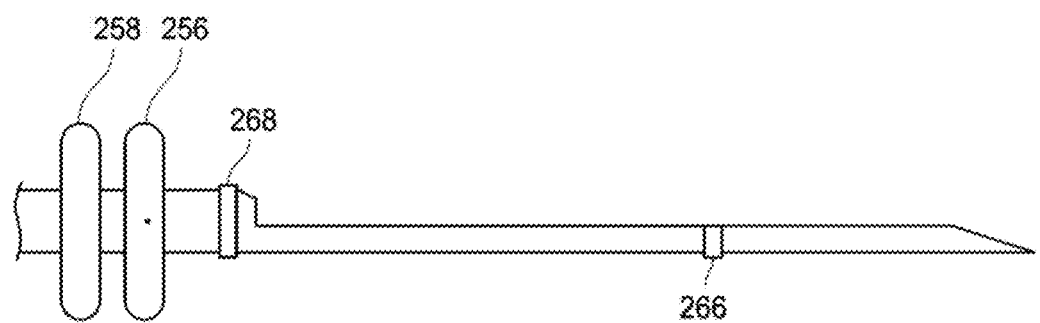
Figure 15C:
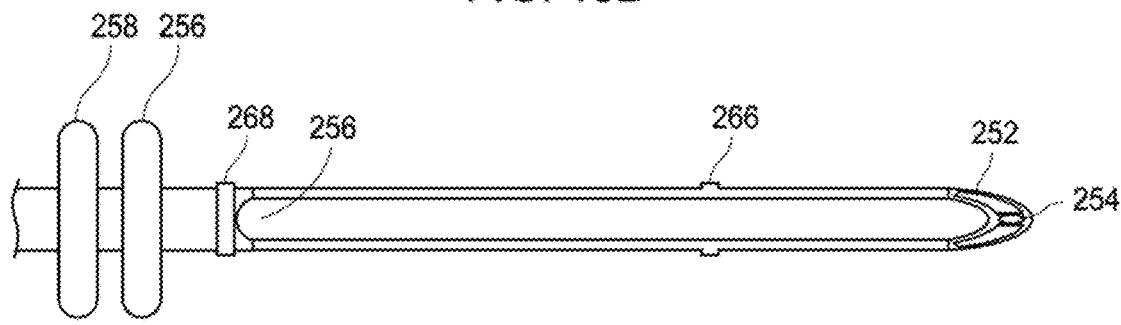

FIG. 15A to FIG. 15C illustrate a perfusion device useful in the procedures described above requiring perfusion of the pericardial space. However, the perfusion device described below is not limited to cardiac applications. Instead, the perfusion device can be used in any application requiring perfusion of a space, cavity or other body structure.

FIG. 15A illustrates a working end of perfusion device. As shown, the working end terminates in a number of fluid delivery lumens 252. The fluid delivery lumens 252 can be coupled to a fluid source at a proximal end of the perfusion device 250. In use, the perfusion device 250 supplies normal or cooled saline or other fluid to the pericardial space. The perfusion device 250 can optionally include a guide wire lumen 252.

The perfusion device 250 removes fluid via lumen 256. Accordingly, the proximal end of evacuation lumen 256 can be coupled to a vacuum source or fluid collecting chamber at the proximal end of the device 250. As shown, the fluid delivery lumens 252 extend further beyond the evacuation lumen 256 to allow for delivery of fluid and perfusion of the fluid at the target site. The fluid is removed only once the fluid reaches the evacuation lumen 256. In some cases, the pericardium can fill with fluid before fluid leaves through the evacuation lumen 256. The flow of fluid out of the fluid delivery lumens 252 and into the pericardial space can be controlled to maintain hemodynamic stability.

FIG. 15A also illustrates the perfusion device 250 as optionally including one or more balloons 258 and 260 or expandable anchors. As shown below, the balloons 258 and 260 can be inflated to secure about the pericardium to secure the device to the pericardium while creating a seal at the pericardial incision. FIGS. 16B and 15C illustrate side and top views respectively of the fluid perfusion device 250. The figures also illustrate the perfusion device 250 as having radiopaque markers 266 and 268. While the drawings show two markers, any number of markers can be used.

Figure 16A:
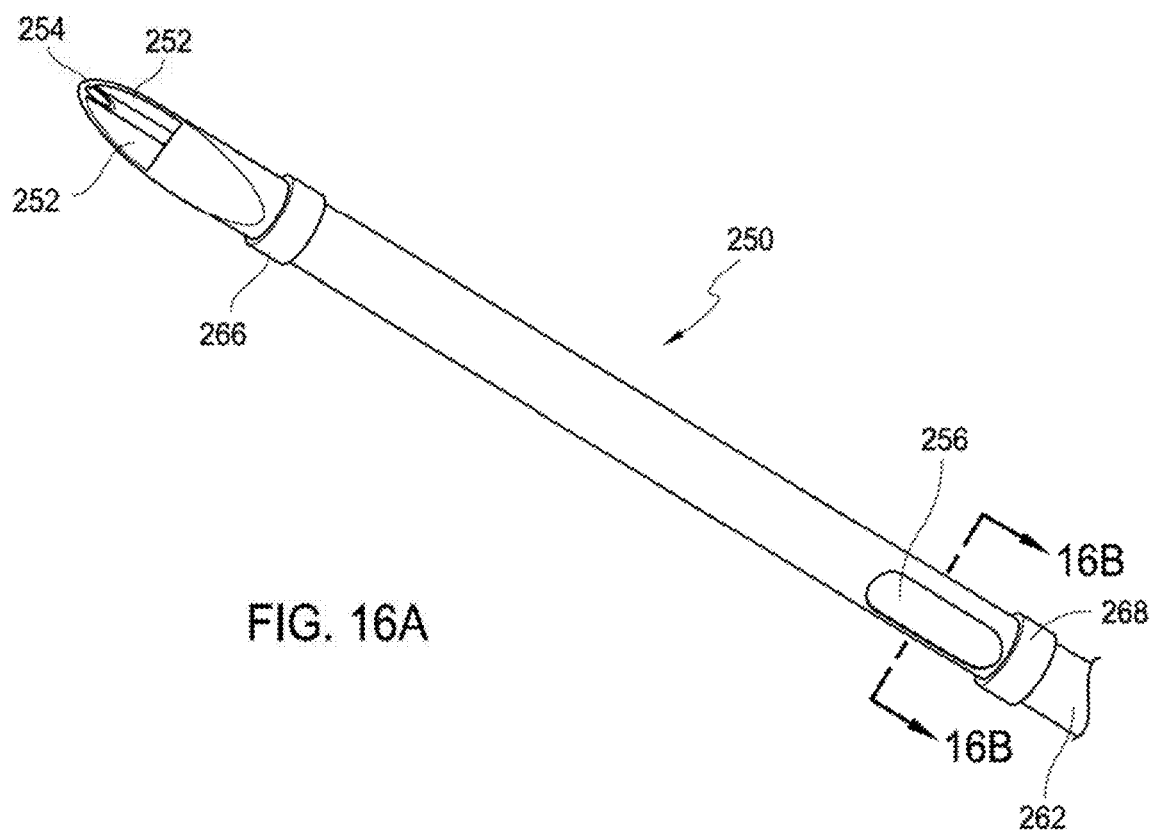
FIG. 16A to FIG. 16B show a second variation of a perfusion device and a cross-sectional view of the shaft of that device.
Figure 16B:
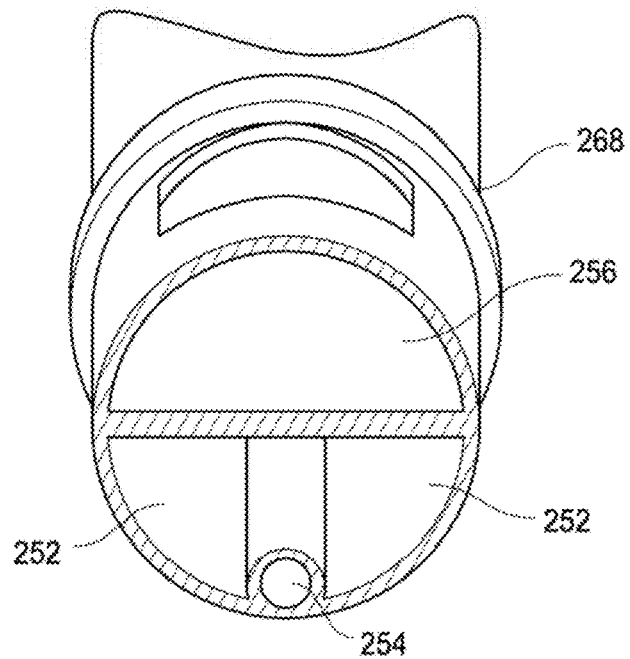

FIGS. 16A and 16B illustrate another variation of a perfusion device 250. In this variation, the evacuation lumen 256 does not extend to the end of the device 250. In addition, the device 250 of FIG. 16A does not include any balloons or anchors.

Figure 17:
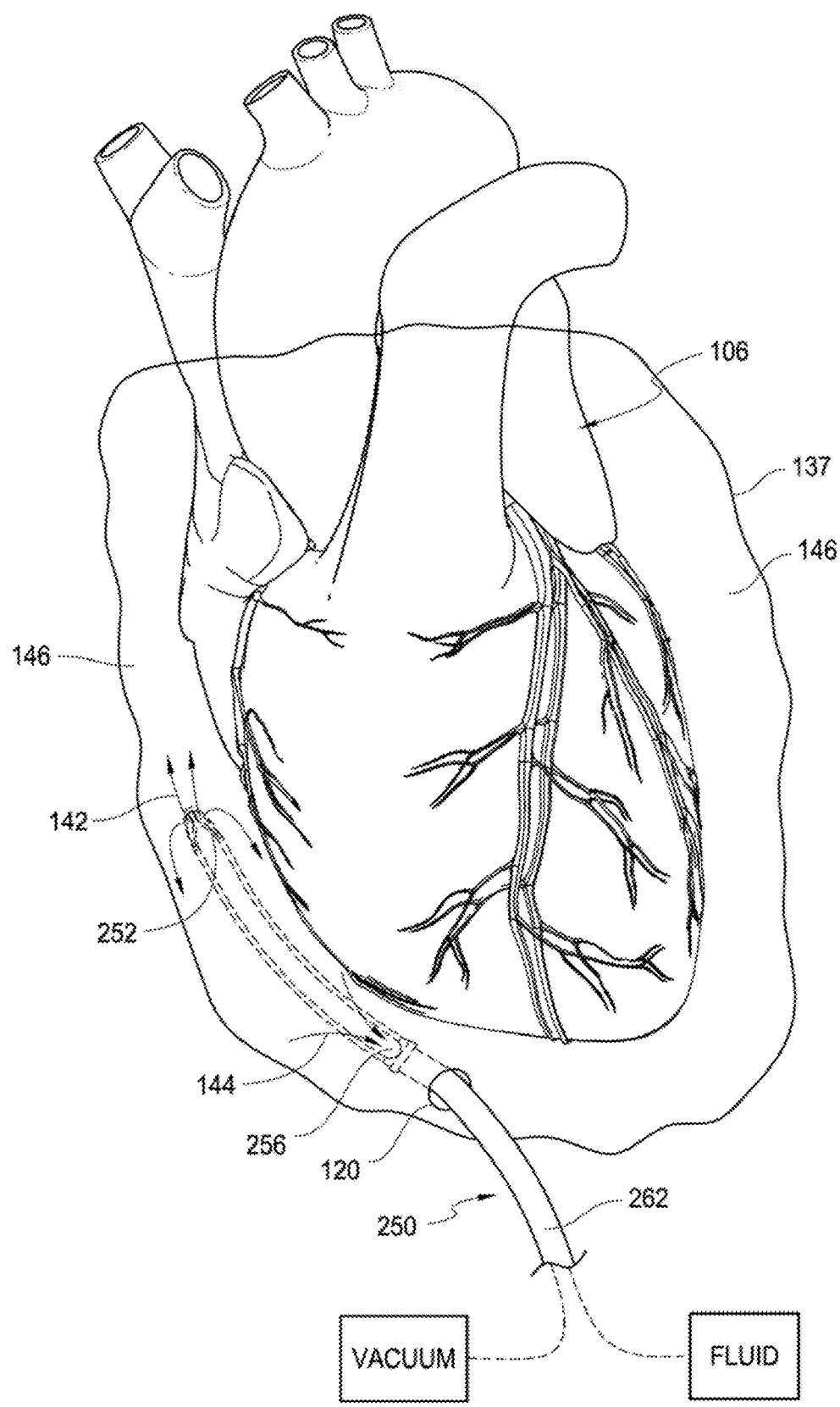
FIG. 17 illustrates a perfusion device secured to the pericardium and perfusing fluid through the pericardial space.

FIG. 17 shows an example of a perfusion device 250 inserted into an opening 120 in the pericardium 137. Clearly, the shaft 262 of the perfusion device 250 can remain flexible to navigate through the body to the pericardial space 146. Once the physician obtains percutaneous access to the pericardial space, the device 250 can deliver room temperature or cooled saline (or any other fluid) to the epicardial space 146. The fluid can be perfused into and through the pericardial space from the fluid delivery lumens 252 as denoted by arrows 142. The fluid is then evacuated at the evacuation lumen 256 as denoted by arrows 144. The evacuation lumen 256 can be driven by a vacuum or by the increased pressure within the pericardial space 146 that results from the delivery of fluid. As shown, the proximal end of the device 250 can be coupled to a vacuum source (or fluid collection unit) as well as a source of fluid.

Perfusing the pericardial space 146 allows the physician to maintain hemodynamic stability. Moreover, the addition of saline or any fluid provides the ability to directly visualize within the pericardial space using scope or similar type device. In addition, the use of fluid can also help increase space between the epicardial surface and the pericardium through fluid distension. Yet another benefit of filling the pericardium is that the fluid can provide cooling to the tissue to prevent collateral damage to adjacent structures from heating due to the use of an ablation device.

FIG. 17 also illustrates the use of an optional guide wire 62 for positioning of the perfusion device 250. The guidewire 62 can be removed prior to delivery of fluid or can remain within the pericardial space 146.

Figure 18A:
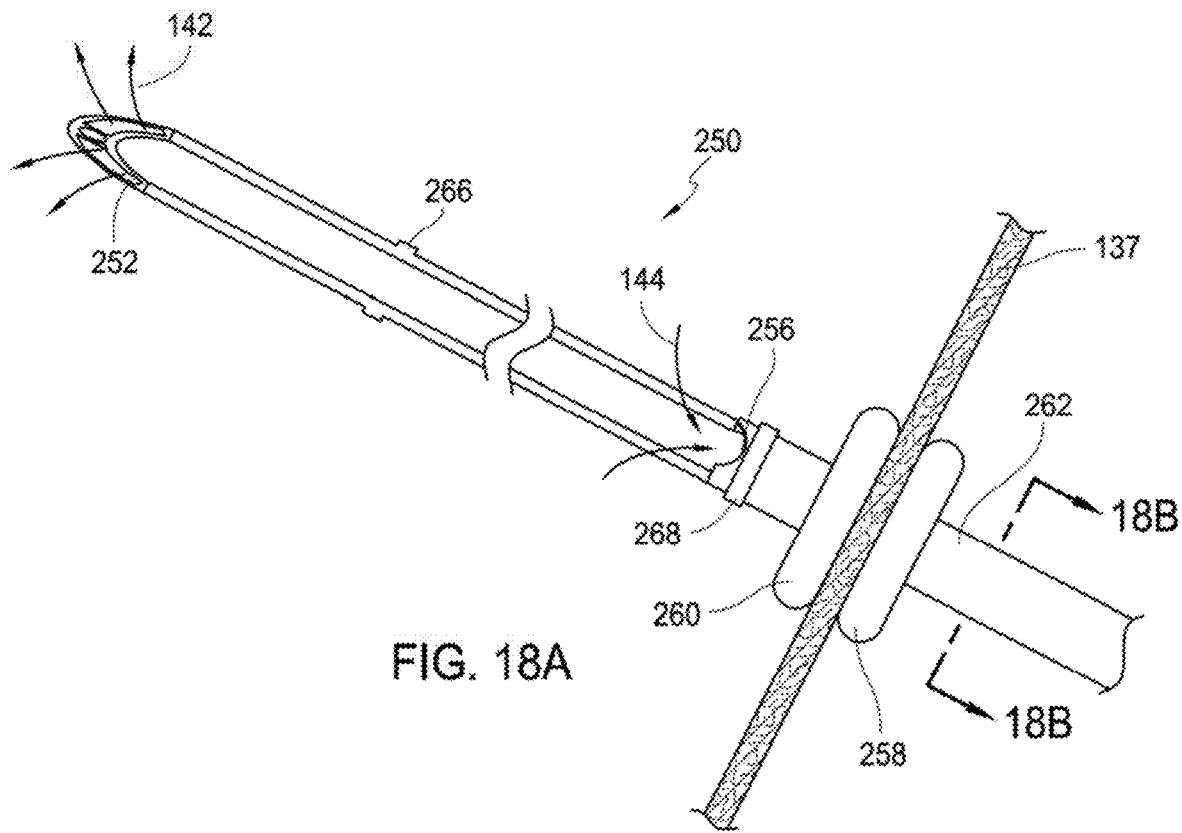
FIG. 18A illustrates a partial cross sectional view of the perfusion device coupled to the pericardium while perfusing fluid.
Figure 18B:
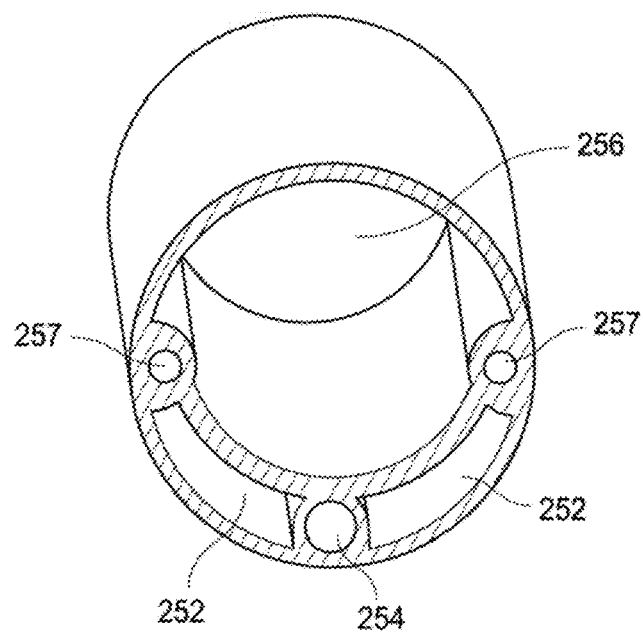
FIG. 18B shows a partial cross sectional view of the shaft of the perfusion device of FIG. 18A.

FIG. 18A illustrates a magnified view of the device 250 secured to the pericardium 137 using the two balloons 258 and 260 as anchors. As shown, fluid delivery 142 occurs through the fluid delivery lumens 252 and the fluid is removed 144 via the evacuation lumen 256. Clearly, the flow of fluid can be reversed (e.g., fluid is provided via lumen 256 and removed via lumen 252). FIG. 18B illustrates a partial cross sectional view of the shaft 262 of the perfusion device 250. As illustrated, this variation includes at least 5 lumens: one lumen 252 for each balloon, the evacuation lumen 256, the fluid delivery lumen 252 and the guide wire lumen 254.

Although the present methods and devices have been described in terms of the embodiments above, numerous modifications and/or additions to the above-described preferred embodiments would be readily apparent to one skilled in the art. It is intended that the scope of the present inventions extend to all such modifications and/or additions and that the scope of the present inventions is limited solely by the claims of the invention.

What is claimed is:

1. A method of creating a lesion on a surface of a heart in a body of a patient, the method comprising:
   creating an incision to access a chest cavity of the patient;
   creating an opening in a pericardium of the patient and positioning an access device with a dilation device into the pericardial space;
   creating a path within the pericardial space by positioning the dilation device within a desired location in the pericardial space prior to dilating the pericardium and subsequently dilating the pericardium at a plurality of locations such that the plurality of locations form the path;
   advancing a treatment device through the path to position the treatment device against a surface of the heart; and
   creating the lesion on the surface of the heart using the treatment device.

2. The method of claim 1, further comprising advancing a guide wire into the pericardial space and where positioning the dilation device into the pericardial space comprises advancing the dilation device over the guidewire.

3. The method of claim 2, further comprising withdrawing the dilation device from the guidewire, and where advancing the treatment device comprises advancing the treatment device over the guidewire.

4. The method of claim 2, where the guidewire comprises a steerable guidewire, the method further comprising steering the guidewire to advance the guidewire.

5. The method of claim 1, further comprising expanding the dilating device during creating of the lesion to separate an anatomical structure from the heart surface.

6. The method of claim 5, where the anatomical structure comprises a structure selected from a phrenic nerve or an esophagus.

7. The method of claim 1, further comprising cooling tissue using the dilation device before, during or after creating of the lesion.

8. The method of claim 1, where the dilation device comprises a fluid expandable balloon.

9. The method of claim 1, where the dilation device comprises a mechanically expandable structure.

10. The method of claim 1, further comprising delivering a fluid to the pericardial space.

11. The method of claim 10, where delivering the fluid to the pericardial space comprises maintaining a fluid layer between the heart surface and the pericardium.

12. The method of claim 11, where maintaining the fluid layer between the heart surface and the pericardium comprises cooling the surface of the heart.

13. The method of claim 11, further comprising advancing a visualization device into the fluid layer to maintain visualization of the surface of the heart during creating the lesion.

14. The method of claim 11, further comprising delivering a contrast agent to the pericardial space.

15. The method of claim 11, further comprising delivering a medicament substance to assist in healing of heart tissue.

16. The method of claim 1, further comprising remotely tracking the dilation device to localize a position of the dilation device from outside the body of the patient.

17. The method of claim 1, where the treatment device comprises a steering mechanism and where advancing the treatment device comprises steering the treatment device.

18. The method of claim 1, further where the dilation device is coupled to the treatment device.

19. The method of claim 1, further where the dilation device is coupled to a guidewire.

20. The method of claim 1, where the treatment device comprises an opening exposing an electrode, the treatment device also comprising a vacuum lumen in fluid communication with a vacuum source and a fluid perfusion lumen fluid communication with a fluid source, where both the vacuum lumen and fluid perfusion lumen are fluidly coupled to the opening.

21. The method of claim 20, further comprising drawing a vacuum in the vacuum source to cause a drop in pressure in both the vacuum lumen and the opening, whereupon placing the opening against a soft tissue of the surface of the heart creates a seal against the soft tissue to cause the fluid perfusion lumen to drop in pressure resulting in fluid flow from the fluid source through the fluid perfusion lumen across the opening and through the vacuum lumen, where when uncovered the opening prevents the perfusion lumen from reducing in pressure and preventing fluid flow.

22. The method of claim 20, where creating the lesion on the surface of the heart comprises applying RF energy to using the electrode to create a contiguous transmural lesion in atrial tissue of the heart.

23. The method of claim 22, where creating the contiguous transmural lesion comprises creating a series of contiguous transmural lesions.

24. The method of claim 22, where advancing the treatment device comprises advancing the treatment device to a plurality of regions to create a pattern of lesions on the surface of the heart.

25. The method of claim 20, where advancing the treatment device to the irregular surface of the soft tissue comprises advancing the treatment device during a procedure selected from the group consisting of an arthroscopic, laparoscopic, and other minimally invasive procedure.

26. The method of claim 20, where creating the lesion on the surface of the heart comprises applying vibrational energy to the electrode to create a contiguous transmural lesion in atrial tissue.

27. The method of claim 20, where the electrode has a length and conforms to the surface of the heart to create a curvilinear lesion.

28. The method of claim 20, where the portion of the treatment device housing the electrode is pre-shapeable to assume a shape and where the lesion forms in the shape.

29. The method of claim 20, further comprising advancing a track adjacent to the irregular surface and where advancing the treatment device to the irregular surface comprises advancing the treatment device over the track.

30. The method of claim 29, where the track comprises a device selected from the group consisting of a wire, a steerable catheter, a steerable guide-wire, a shaped tube, and a shaped mandrel.

* * * * *